US009730655B2

(12) United States Patent
Stark et al.

(10) Patent No.: US 9,730,655 B2
(45) Date of Patent: Aug. 15, 2017

(54) METHOD FOR IMPROVED DETECTION OF NODULES IN MEDICAL IMAGES

(71) Applicants: Tracy J. Stark, Plano, TX (US); Daniel J. Ferlic, White Bear Lake, MN (US)

(72) Inventors: Tracy J. Stark, Plano, TX (US); Daniel J. Ferlic, White Bear Lake, MN (US)

(*) Notice: Subject to any disclaimer, the term of this patent is extended or adjusted under 35 U.S.C. 154(b) by 65 days.

(21) Appl. No.: 14/159,144

(22) Filed: Jan. 20, 2014

(65) Prior Publication Data
US 2014/0205163 A1 Jul. 24, 2014

Related U.S. Application Data

(60) Provisional application No. 61/754,800, filed on Jan. 21, 2013.

(51) Int. Cl.
A61B 6/12 (2006.01)
A61B 6/00 (2006.01)
A61B 6/03 (2006.01)
A61B 5/055 (2006.01)
A61B 5/00 (2006.01)

(52) U.S. Cl.
CPC ............... A61B 6/12 (2013.01); A61B 6/461 (2013.01); A61B 6/467 (2013.01); A61B 6/50 (2013.01); A61B 5/055 (2013.01); A61B 5/748 (2013.01); A61B 6/03 (2013.01); A61B 6/468 (2013.01); A61B 6/469 (2013.01); A61B 6/502 (2013.01); A61B 2576/00 (2013.01)

(58) Field of Classification Search
None
See application file for complete search history.

(56) References Cited

U.S. PATENT DOCUMENTS 5,664,081 A * 9/1997 Saito .............................. 345/619
6,983,063 B1 * 1/2006 Novak et al. ................. 382/131
8,655,072 B2 * 2/2014 Kimoto ......................... 382/173

(Continued)

OTHER PUBLICATIONS

Suneetha et al., Enhancement Techniques for Gray scale Images in Spatial Domain, Apr. 2012, International Journal of Emerging Technology and Advanced Engineering, vol. 2, Issue 4, p. 14.*

(Continued)

Primary Examiner — Sumati Lefkowitz
Assistant Examiner — Jiangeng Sun
(74) Attorney, Agent, or Firm — Kinney & Lange, P.A.

(57) ABSTRACT

Special displays of medical images are generated that help a radiologist better detect nodules by exploiting the inherent human visualization abilities of detection of symmetry, asymmetry, motion and relative motion. A Region of Interest (ROI) on an x-ray (mammogram, CT-scan, MRI, or other medical image) is selected and the data within the ROI is copied such that a new display now has two or more copies of the information within the ROI. This copy may contain the same relative positions as the original image, or may be a mirror image of the original data. The ROI is moved over the medical image in search of nodules. This movement can be random, under the direct control of the radiologist, systematically moved by a computer algorithm, or some combination of the above.

15 Claims, 22 Drawing Sheets

(56) References Cited

U.S. PATENT DOCUMENTS

| | | | |
|---|---|---|---|
| 2004/0100503 A1* | 5/2004 | Morita | A61B 6/463 715/804 |
| 2004/0184644 A1* | 9/2004 | Leichter et al. | 382/128 |
| 2004/0184647 A1* | 9/2004 | Reeves et al. | 382/131 |
| 2004/0208385 A1* | 10/2004 | Jiang | 382/254 |
| 2006/0004282 A1* | 1/2006 | Oosawa | 600/416 |
| 2007/0274578 A1* | 11/2007 | Doi et al. | 382/128 |
| 2007/0286469 A1* | 12/2007 | Yamagata et al. | 382/131 |
| 2009/0016491 A1* | 1/2009 | Li | 378/98.5 |
| 2009/0257657 A1* | 10/2009 | Temmermans | G06T 3/0075 382/195 |
| 2009/0310843 A1* | 12/2009 | Moriya | 382/131 |
| 2010/0189323 A1* | 7/2010 | Sakagawa | 382/128 |
| 2010/0226550 A1* | 9/2010 | Miyasa et al. | 382/128 |
| 2010/0250275 A1* | 9/2010 | Sakagawa et al. | 705/2 |
| 2013/0129171 A1* | 5/2013 | Sohn et al. | 382/131 |

OTHER PUBLICATIONS

Fisher et al., Point Operations—Contrast Stretching, Jun. 24, 2004.*
Czech Technical University in Prague, Linear Filtering and Filter Design (Image Processing Toolbox), Oct. 25, 2007.*

* cited by examiner

METHOD FOR IMPROVED DETECTION OF NODULES IN MEDICAL IMAGES

CROSS-REFERENCE TO RELATED APPLICATION(S)

This application claims the benefit of Provisional Application Ser. No. 61/754,800, filed Jan. 21, 2013, entitled METHOD FOR IMPROVED DETECTION OF NODULES IN MEDICAL IMAGES, by Tracy J. Stark and Daniel J. Ferlic. U.S. Provisional Application Ser. No. 61/754,800 is incorporated by reference herein.

BACKGROUND

Lung cancer is the second most common cancer among both men and women. With an overall mortality rate of about 90%, it is the leading cause for cancer deaths for both sexes. Survival from lung cancer is directly related to its size when it is detected. The earlier the detection is, the higher the chances of successful treatment are. The cure rate for Stage I lung cancers is 70-80%. By the time the nodules grow large enough for them to interfere with a patient's breathing, then the time for optimum treatment has passed.

These types of cancers can be detected using medical imaging such as X-rays and CT-scans. They appear as "nodules", bright circular abnormalities in the X-ray image. Nodules are normally denser than their surrounding tissues. They can vary in size, intensity and contrast levels. On the x-ray they can appear to be located between ribs, on top of ribs, or behind an organ such as the heart.

Most lung nodules do not have any symptoms and are found "accidentally" when a chest x-ray is done for some other reason. When present, these nodules represent cancer about 40% of the time. This percentage is higher in those that are at high risk for lung cancer. The larger the nodules are, the easier they are to detect, and the higher the probability they are due to cancer. The smaller the nodules are, the harder they are to detect. 1 cm is close to the current detection limit.

There are a few diagnostic characteristics that can be used to determine if a nodule is cancerous or not. The larger the nodule, the more likely it is cancerous. Cancerous nodules on average double in size in about 4 months, whereas benign nodules have little or no size change in the same period. Therefore, nodules that grow rapidly are most likely cancerous. The rougher their edges, or the larger they are, the more likely they are to be cancerous. Smooth, round nodules are more likely to be benign, whereas irregular or "spiculated" nodules are more likely to be cancerous. Lung nodules that are calcified are more likely to be benign. Also, lung nodules described as "cavitary," meaning that the interior part of the nodule appears darker on x-rays, are more likely to be benign.

It is estimated that somewhere between 10 to 20% or more of cancerous chest X-ray nodules are missed on the first reading of the film. The smaller the nodule, the higher the percentage of them are missed. When a second X-ray is taken, and the nodule has grown, then looking back at the earlier X-rays it is normally obvious that the nodule was present, but was missed by the radiologist.

The early detection and diagnosis of pulmonary nodules in chest X-ray image are among the most challenging clinical tasks performed by radiologists. They may or may not seek the aid of methods to digitally enhance the x-rays or automatically detect potential nodules. In test x-rays, current automatic detection methods typically do not identify all known nodules. If their parameters are set such that they do detect all known nodules, then they also will detect many nodules that are false (false positives). How to reduce the number of false positives while maintaining a high true positive detection rate is the most important work in realizing a chest CAD system.

It is apparent that a method to accurately and routinely detect smaller and/or a higher percentage of nodules in chest X-rays, CT-scans, or mammograms has the potential to save lives. We want to detect them when they are small since they can grow so quickly, and that chest x-rays are not taken that often. A lung cancer screening method that can safely and economically detect a large number of potentially curable Stage I lung cancers would be an important public health development. The purpose of this invention is to provide such a technique.

It has been observed that the human visual system in most individuals is very good at detecting symmetry and variations from symmetry within a scene. It is also good at detection of motion and relative motion of objects within a scene.

If you drop a small object on the floor, you might pick up a similar object and drop it as well, watching and listening as it falls. By dropping the known object, we can see (and hear) how it falls, and understand what it looks like against the floor background. Having this reference, and/or the symmetry of two objects on the floor helps in locating the first object. One of the aspects of this invention is to take advantage of the human visual system to see symmetry, asymmetry, and duplicate objects.

The advertising industry takes advantage of the human visualization system's ability to detect subtle and differential motion. For example, in a TV advertisement they will slowly enlarge and move text that they want the viewer to pay the most attention to. We can't help but see the movement, and our attention is drawn to the area of the display where the movement occurs. Differential movement at the same location in a display appears to be more powerful in attracting our attention than just simple movement of one object. This is another feature of the human visualization system that the current invention can capitalize on.

SUMMARY

This invention attempts to capitalize or exploit our inherent human visualization abilities of detection of symmetry, asymmetry, motion and relative motion by generating special displays that will help a radiologist better detect nodules. This application will focus on the application of these display techniques to chest x-rays. However, the method can also be applied to mammograms, CT-scans, MRI and other medical imaging modalities.

A Region of Interest (ROI) on an x-ray (mammogram, CT-scan, MRI, etc) is selected and the data within the ROI copied such that a new display now has two or more copies of the information within the ROI. This copy may contain the same relative positions as the original image, or may be a mirror image of the original data.

In the current investigations using this method, a rectangular ROI is optimum, but is not a requirement of the invention. Displaying the copy of the data as a mirror image using a "flat" mirror produces the best result. Again the data could just be copied, or a curved mirror could be used, but with our current investigations these will not produce as good of results. A vertical ROI approximately 1 inch wide is a good default that can be overridden by the radiologist.

The ROI is moved over the x-ray in search of nodules. This movement can be random, under the direct control of the radiologist, systematically moved by a computer algorithm, or some combination of the above. The systematic movement by a computer algorithm, which can be overridden by the radiologist, appears to be the best use of this technique.

Initially moving a thin vertical rectangular ROI (with a single mirror surface) systematically from left to right, and then reversing the direction of motion when the edge of the x-ray is reached appears to be a good default motion. If the mirror is on the right side of the ROI and the ROI is moving from left to right, the nodules will appear to grow from the center of the display, under go "cell division", and then move horizontally until they leave the outer edges of the ROI. Anatomical structures appear to move along non-horizontal paths. When the direction of the ROI movement is reversed, the nodules will appear at each edge of the ROI, and move along a horizontal line exhibiting what could be called "cell collision" or "cell fusion".

If the mirror surface is on the left side of the ROI, then "cell collision" will occur when moving from left to right, and cell division will occur when moving from right to left.

The ROI needs to be moved a small amount (relative to both the size of the nodule and the width of the ROI), in a short period of time, for optimum "cell collision" or "cell division" visual effect. Such a display method could be considered a movie loop type of animation.

The invention does not require a movie loop type of animation, but some of the best results are obtained when used in this manner. The radiologist could change the position of the ROI in larger steps and use a larger time delay between frames (displays). This would be analogous to a slide show type of presentation. Each new ROI position could be under program control, or user control by clicking the mouse for example.

When changing the position, it is best to have some overlap between the two images. With the movie method, the overlap is the entire ROI except for one or two pixels. In a slide show method, the overlap may be for example ¼, ⅓, or ½ of the width of the ROI in the direction of motion.

Using a slide show type of movement, the symmetry and changes in symmetry are what provide ability to better detect the nodules. When using a movie mode type of movement, both the symmetry of the nodules and the apparent relative motion of the nodules in relationship to the anatomical features increases the human ability to detect the nodules.

The phrase "anatomical features" refers to such things as blood vessels, bronchial, bones and organs. Circular nodules will have an apparent motion that is perpendicular to the mirror. Other anatomical features will appear to move in a direction that is related to the angle at which they intersect the mirror.

Note in the above the use of the verb "appears". This motion observed is a type of visual or optical illusion due to the movement of the mirror plane.

The figures will illustrate a ROI as a vertical strip, however this should not limit the scope of the invention, but only provide one example. The method applies the same for using a horizontal strip, a strip at an arbitrary orientation, a rectangular box that is not the same size as either dimension of the X-ray or some other arbitrary shape.

The method can also be used on data that has undergone some sort of modification, such as digital filtering. For instance, the application of a local amplitude normalization, or automatic gain control has been observed to improve the ability of CAD systems in detecting nodules. This or some other type of image refinement can be applied prior to generating the duplicate images. Applying filters that enhance circular features and reduce linear features would also be useful.

The invention is best implemented using a computer program and a high-resolution display system. The computer program can be written in any of the currently available languages such as C, C++, C#, or Java. A plug-in to the ImageJ software (http://rsbweb.nih.gov/ij/) was written in Java to provide a prototype of the invention. This prototype was used to generate the figures used in this patent application.

BRIEF DESCRIPTION OF THE DRAWINGS

FIG. 14 illustrates using two mirror surfaces instead of one with refine on.

FIG. 15 illustrates using two replication surfaces with refine on.

FIG. 19 illustrates moving the mirror surface across the x-ray to see a nodule undergoing "cell division", without the refine option being on.

FIG. 20 illustrates moving the mirror surface across the x-ray to see a nodule undergoing "cell division", with the refine option being on.

DETAILED DESCRIPTION

Figure 1:
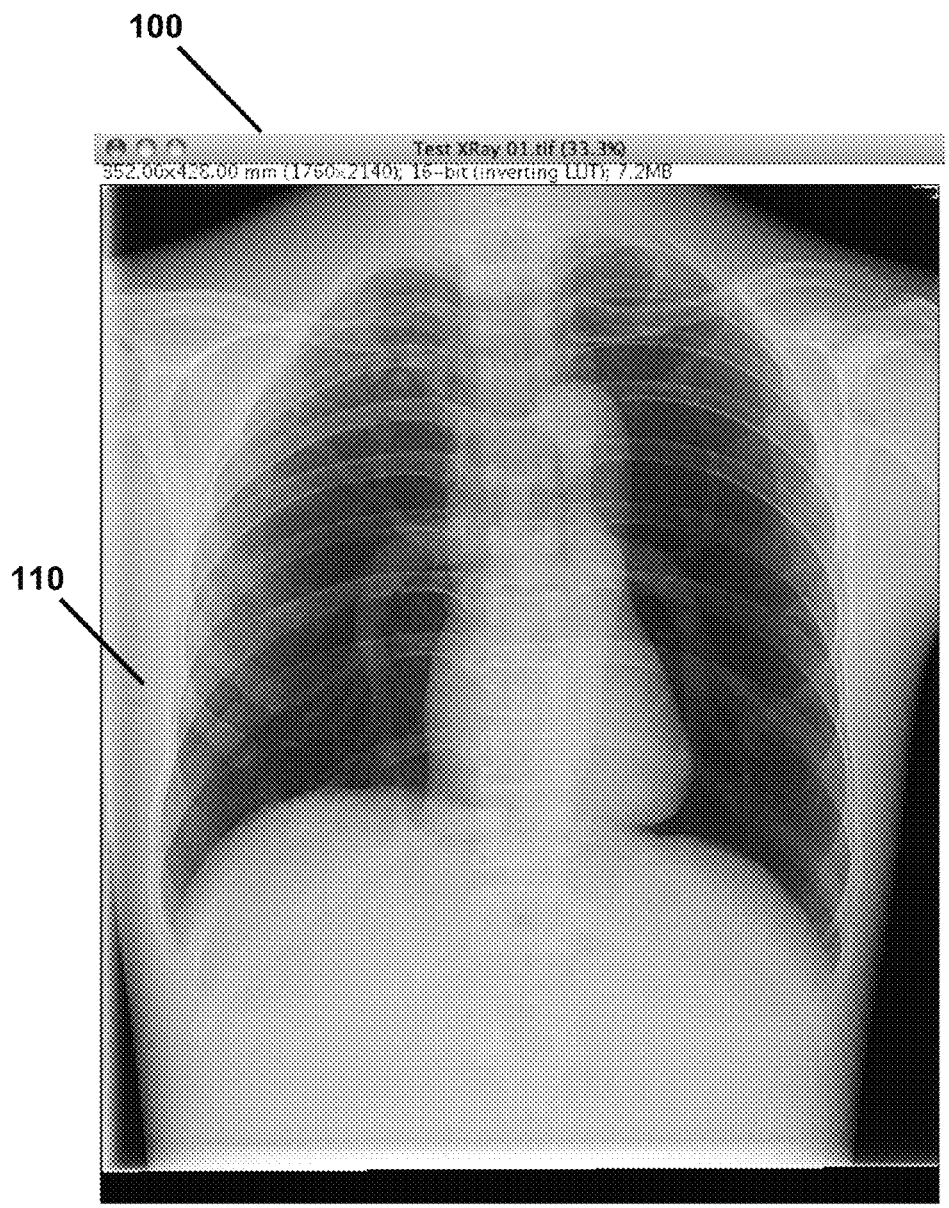
FIG. 1 illustrates a state of the art chest x-ray display method.

The following detailed descriptions can be read in connection with the accompanying drawings in which like numerals designate like elements and in which:

FIG. 1 illustrates a state of the art chest x-ray display method. The chest x-ray 110 is displayed inside of a window frame 100. In this example the public domain program ImageJ (http://rsbweb.nih.gov/ij/) was utilized. The program has a user interface system that is not shown. Radiologists will look at digital chest x-rays 110 using a program such as this. Film x-rays are displayed using a light box. This invention concerns a method of display for digital x-rays. Film x-rays can be digitized to utilize this invention.

Figure 2:
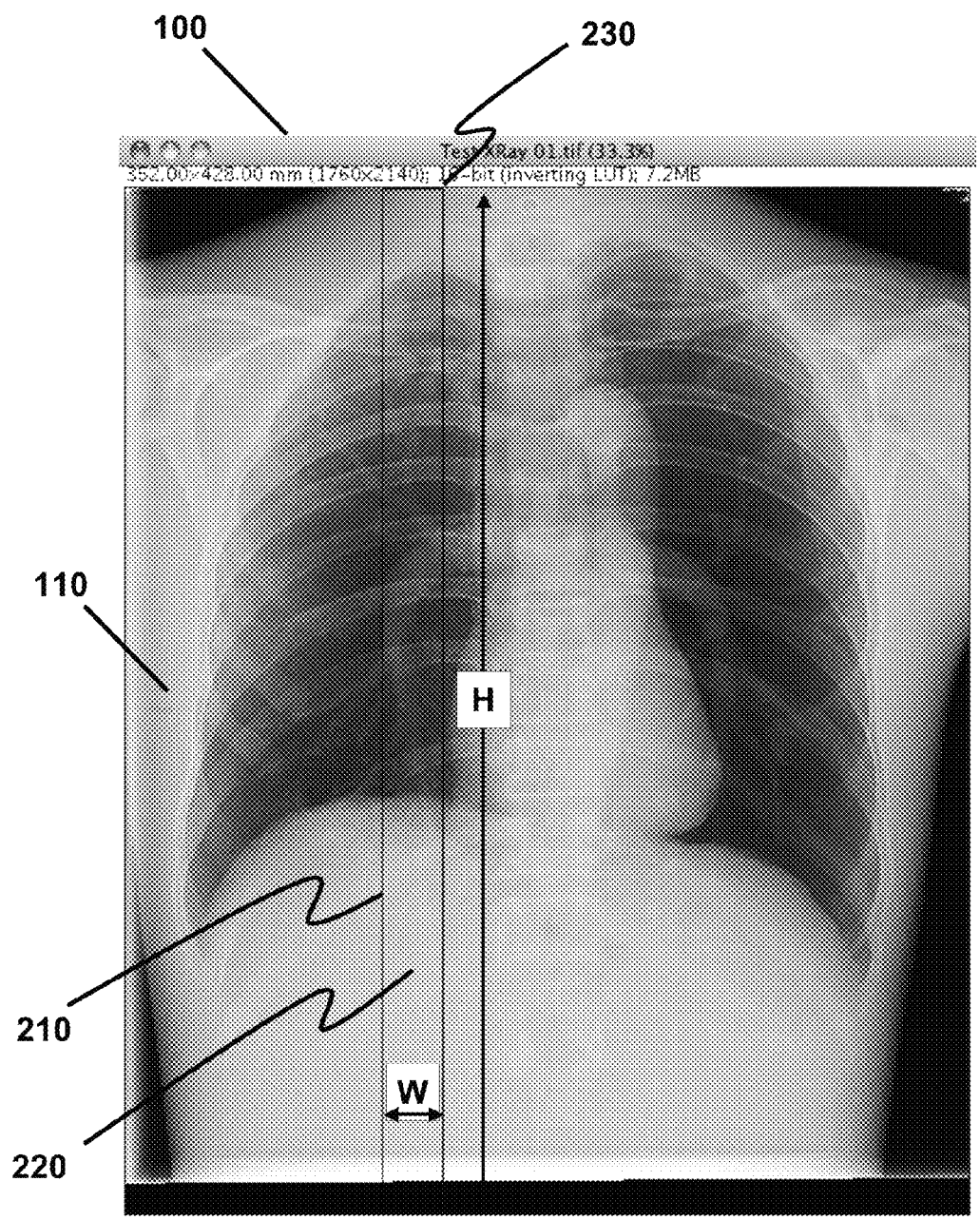
FIG. 2 illustrates a region of interest denoted on a chest x-ray.

FIG. 2 illustrates a Region Of Interest (ROI) 220 denoted on a chest x-ray 110. In this display the ROI is marked with a box 210. The line size, line style, opacity, color and other graphic attributes of this ROI box 210 is something that could be changed by the user. Marking the ROI box 210 on the x-ray 110 is not a requirement of the invention, but doing so is convenient and helps the radiologists orient themselves. The ROI 220 shape can either use a program default, or be defined by the radiologist. In this case, the ROI 220 is a vertical rectangle of width W and height H. The optimum shape of the ROI 220 is either a vertical rectangle as displayed here, or a horizontal rectangle in which H would be about the same value as the current W, and W would be such that it extends the width of the x-ray. A symmetry or replication axis 230 is associated with the ROI 220. In the case of a mirror type display, 230 will represent a symmetry axis. If the data are not mirrored, then 230 will be considered a replication axis. Normally 230 will be a straight line and be along either of the longest sides of the rectangular ROI 220. If the ROI 220 is some arbitrary shape then the replication axis will be a portion of the irregular shape boundary. It is anticipated that using a non-rectangular (or square) shape for the ROI 220 will produce sub-optimal results. The default value for W could be set to the number of pixels closest to 1 inch of x-ray. The default value for H could be set to the height of the x-ray.

Figure 3:
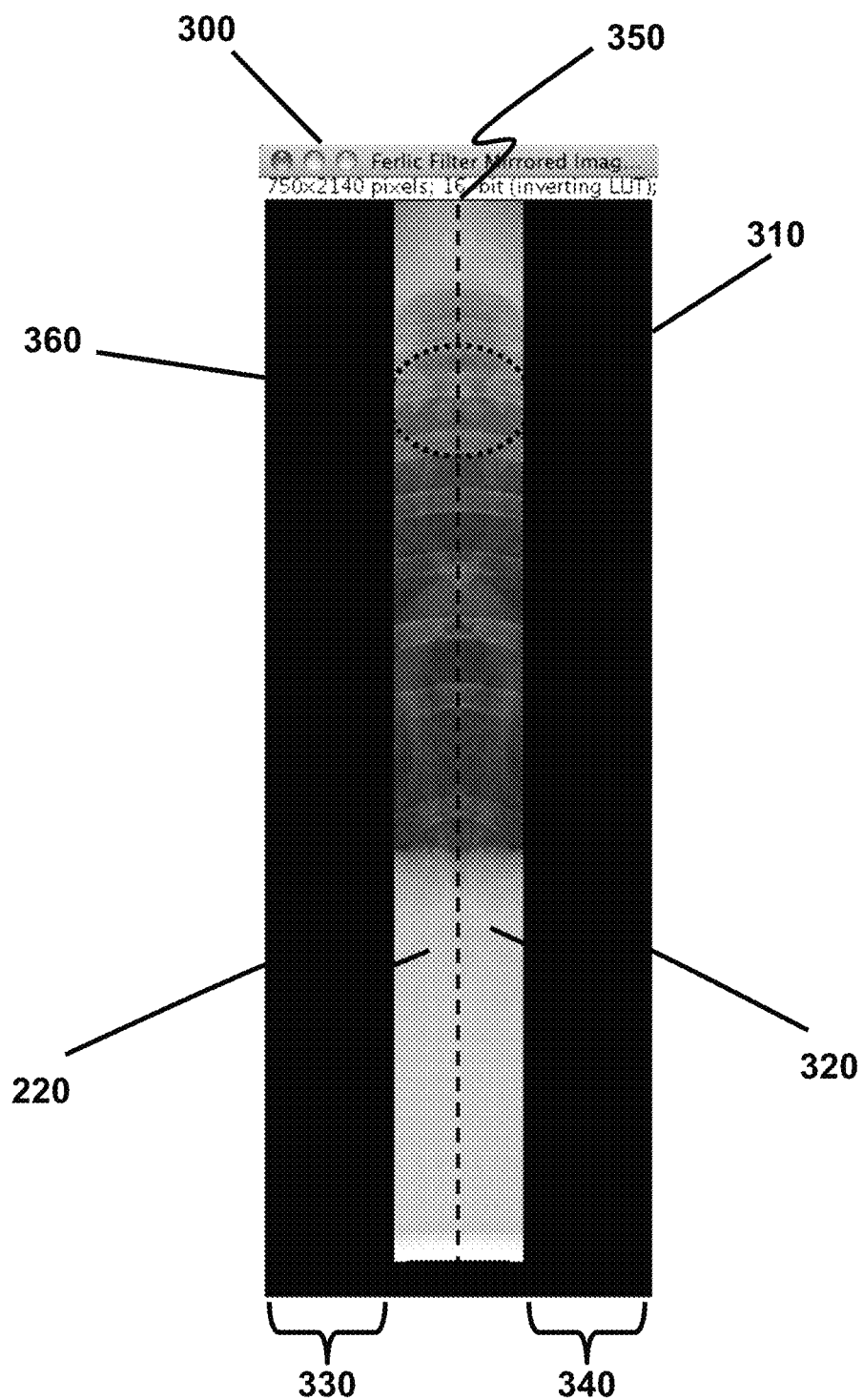
FIG. 3 illustrates a display using one embodiment of the invention.

FIG. 3 illustrates a display using one embodiment of the invention. This display is contained in the window 300. This is a separate window from window 100 that contains the x-ray 110 and ROI outline 220 shown in FIG. 2. The data 310 of the display 300 contains the data from the ROI 220 and a copy of the ROI data 320, along with left 330 and right 340 padding.

In FIG. 3 the left 330 and right 340 padding are of equal width and are equal to twice the width W (seen in FIG. 2) of the ROI. These are good default values. For the sake of symmetry, it is nice to have the left pad width 330 and right pad width 340 to be the same, but the invention will still function if they are of different values. Also the invention will function if their widths are made either larger or smaller than twice the width W (seen in FIG. 2).

The dashed line 350 in this figure marks the axis of symmetry. It is shown here as an example, but normally would not be included in a display used by a radiologist to look for nodules. The user interface could contain a toggle to turn the line on and off. The default setting would be to have it turned off. Line 350 is an axis of symmetry because the data of 320 is a mirror image of that contained in 220. If the data in 320 were the same orientation as that of 220, dashed line 350 would denote a line of replication.

In this embodiment of the invention, the position of the axis of symmetry 350 will not change inside of the window 300 as the ROI 220 is moved about the x-ray data 110 shown in FIG. 2. The data of the x-ray will appear to move relative to the position of the dashed line 350.

The dash oval 360 is used to denote a potential nodule. The radiologist, using a mouse or other user interface implementation, could draw such an oval to record the position of the nodule. If the display were on an iPad, (or other touch screen device) the radiologist could just put his or her finger on the nodule to record its location.

This window 300 would need some sort of user interface. Such a user interface could be similar to 420 shown in FIG. 4. It could be attached to the bottom, side(s), or both, of window 300, or placed in its own separate window. Alternatively its functionality could be placed in pull down menus of the main program. Those versed in the state of the art of computer programming readily know how to create a user interface, so it is not included here. An example of a user interface that might be used by this invention will be provided in subsequent figures. Such a user interface is intended for an example only and should not be construed as limiting the scope of the invention.

Figure 4:
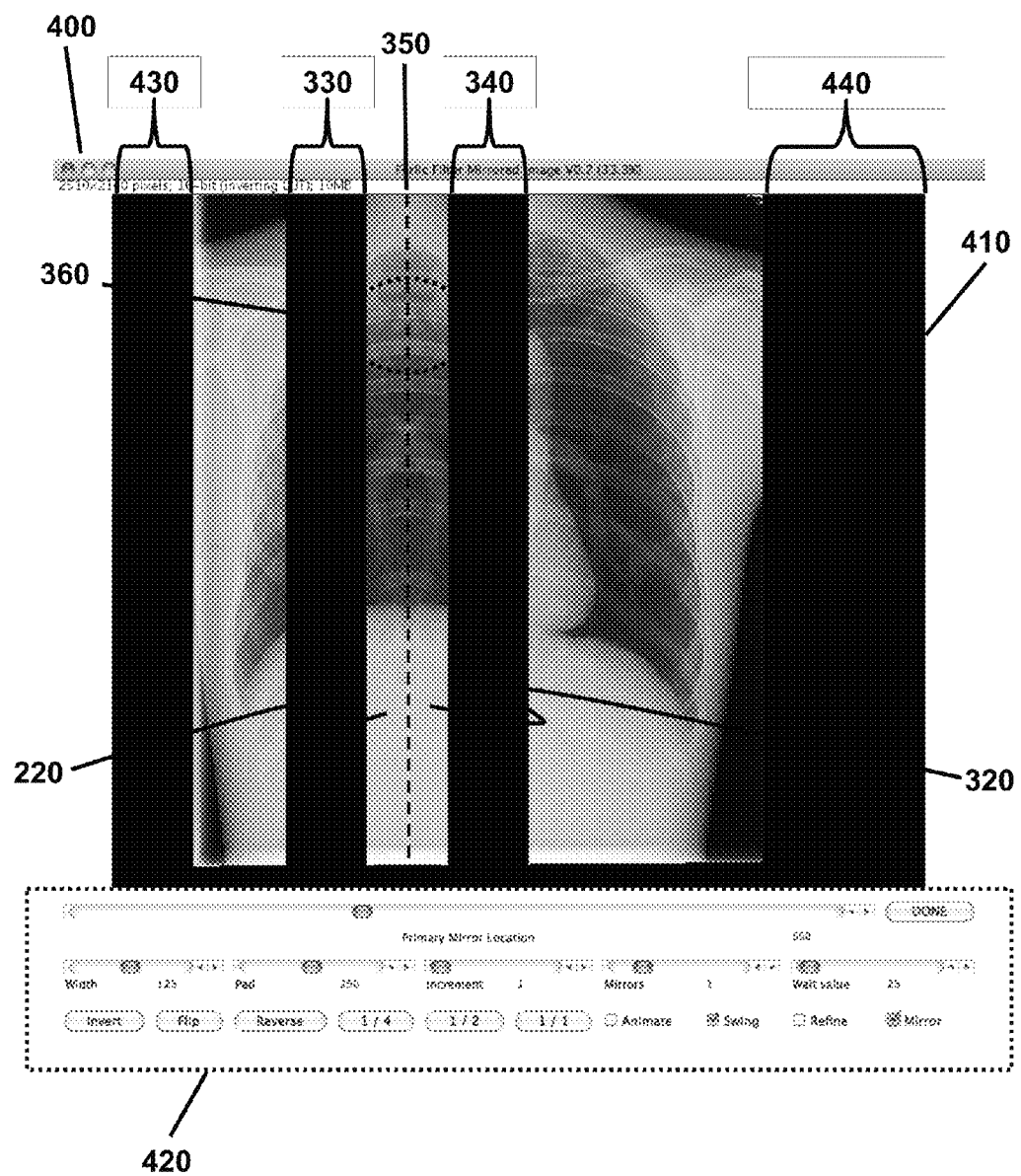
FIG. 4 illustrates a display using another embodiment of the invention.

FIG. 4 illustrates a display using another embodiment of the invention. The display for this embodiment is in its own window 400 just as the previous embodiment. However, in this embodiment the ROI and its replication(s) are displayed relative to the original position of the ROI on the chest x-ray. The data 410 in this display contains padding on the left 430 and padding on the right 440. The default size of the left padding 430 is the same as the padding 330 around the ROI, while the default size of the right padding 440 is the sum of the padding 340, the ROI 220 and the mirrored (or replicated) data 320.

In this embodiment, the axis of symmetry 350 will traverse across the window 400 to mark the relative location of the mirror surface or replication surface as it is moved. As mentioned for the previous figure, the graphic to represent the mirror surface 350 can be under user control. However, normally a line showing the mirror surface would not be displayed. The location is implied by the display itself.

This window 400 has a user interface 420 associated with it. In this example the user interface 420 is placed below the data 410. The widgets within the user interface 420 are provided as examples of some of the variables that could be under user control. Not all of the variables shown need to be under user control, nor are all possible variables that could be within the user interface contained within this example of a user interface. The user interface could be in a separate window, placed in pull down menus, exposed by mouse or key click, or hooked to physical dials and sliders. The example provided here is just an example and should not be considered to limit the invention.

Figure 5:
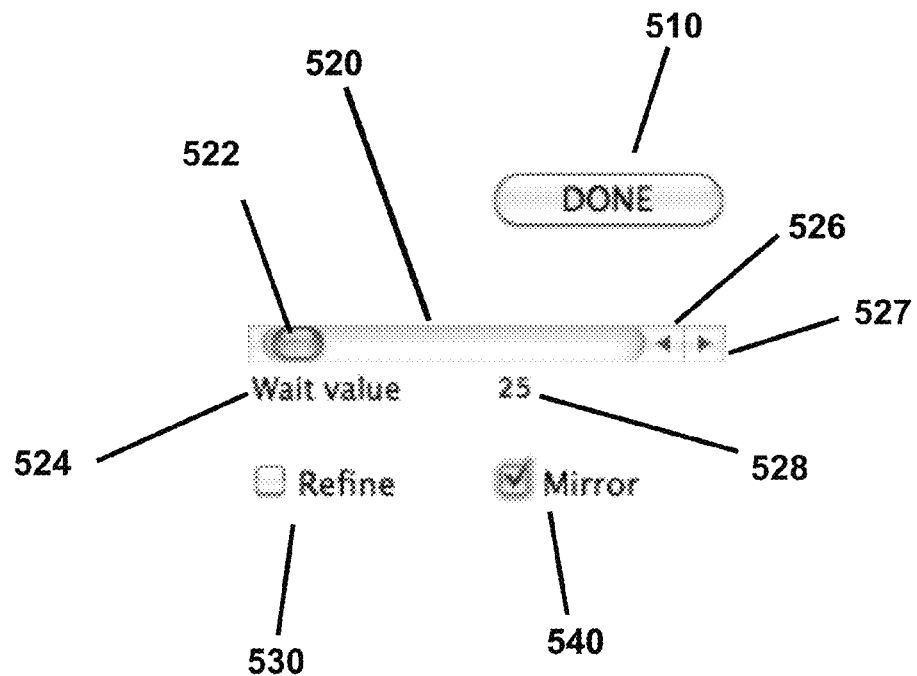
FIG. 5 illustrates a few standard user interface elements.

FIG. 5 illustrates a few standard user interface elements that can be used by this invention. This figure does not illustrate all of the user interface elements that might be used, but only those that are used in the following figures produced from the invention prototype. This figure should not be used to limit the scope of the user interface items that might be associated with the invention. Those skilled in the art of computer programming and using current computer user interfaces will know how to utilize such user interface widgets.

Item 510 is a push button. Clicking on a push button is normally used to causes the program to perform some predefined action. The push button often has a word associated with it to provide a hint as to what action will be performed. In this case "DONE" might signal the program to terminate.

Item 520 refers to a slider bar. Slider bars are used to adjust a particular value. 524 indicates the title of the slider bar, which provides the user a hint as to what the slider bar controls. 528 indicates the current numerical value of the slider bar. In some implementations of a slider bar the user can type a new number in this field to change the value of the slider bar parameter. 522 also indicates the current value of the slider bar parameter, and can also be used to change the current value. 522 provides a relative value from the start to the end of the control range. The control range is defined by the program and may or may not be apparent from the visual implementation of the slider bar. In this example of a slider bar the range is not apparent. The user can use a mouse or other pointing device to change the location of 522, which will then update the value 528. Clicking on the left arrow 526 will decrement the slider value 528 and cause 522 to move to the left by some program-defined increment. Normally the increment is set to one, but this can be any arbitrary number. In some cases another user interface element will be provided to change the increment of a slider bar. Clicking on the right arrow 527 will increment the slider value 528 and cause 522 to move to the right by some program-defined increment. Normally the right and left increments are the same.

Items 530 and 540 are check boxes. They normally are used to change the state of a variable. They contain a check box and a description field. The check box indicates either an "off" status as in 530 or an "on" status as in 540. In 530 the description field contains "Refine" while 540 contains "Mirror". Therefore, in this example the data that are displayed are not in the "Refine" state, but are in the "Mirror" state.

Figure 6:
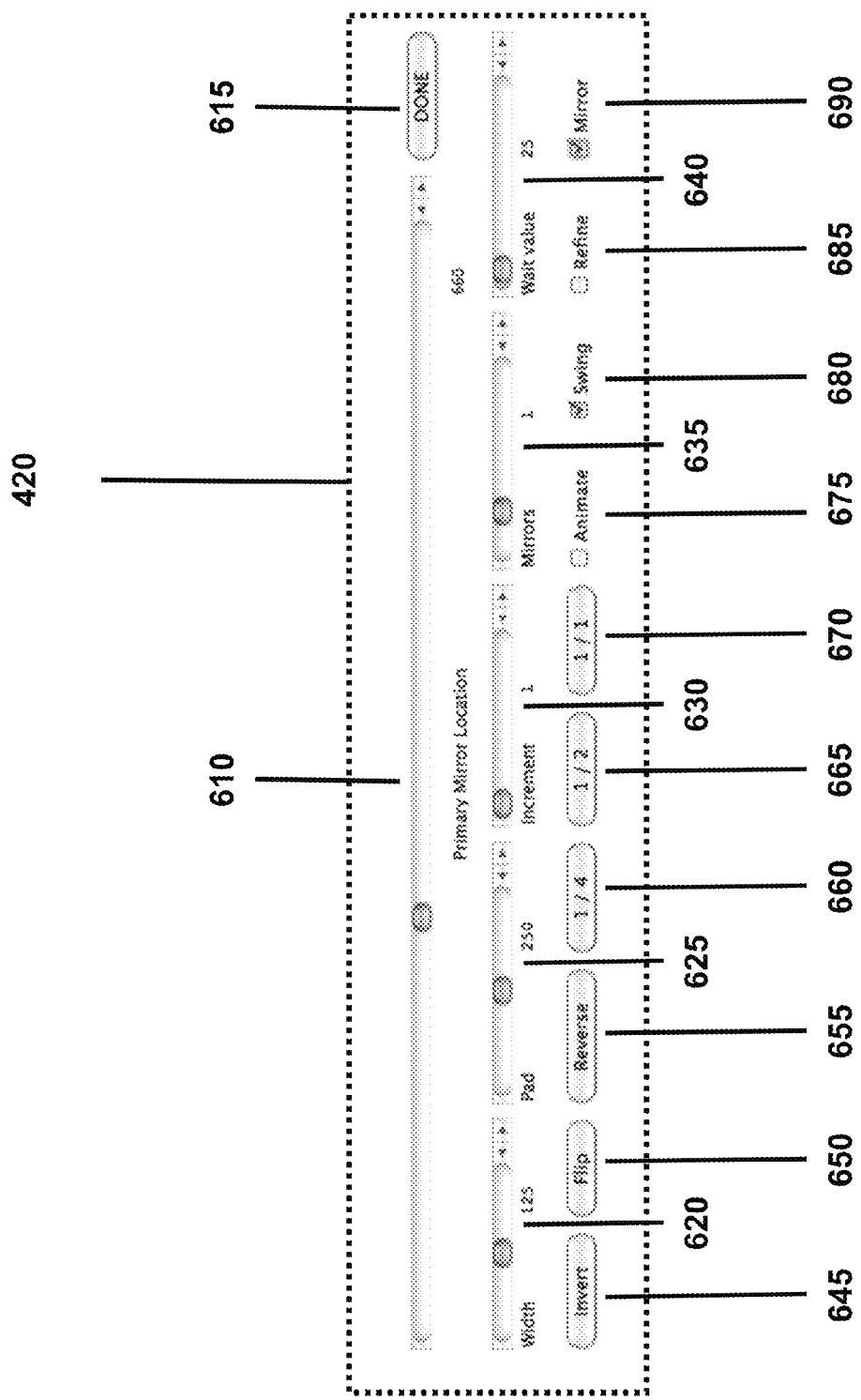
FIG. 6 illustrates the user interface used in a prototype program that implements many aspects of this invention.

FIG. 6 illustrates the user interface 420 used in a prototype program that implements many aspects of this invention. This user interface is composed of three types of widgets: slider bars, buttons and check boxes. These have been described in general in the discussion of FIG. 5. Here we will discuss what each of these elements control for this particular implementation of the invention. This discussion should not be viewed as limiting the scope of the invention, but providing some examples of how it might be used and exploited.

In FIG. 4, and in several subsequent figures, this user interface is shown in conjunction with display 400. It could also be used with the embodiment shown in FIG. 3 as well. It could be attached to the display window, or be in its own display window. The layout of the widgets could be changed, more added, and some removed to better fit the needs of the Radiologist.

Slider bar 610 controls the "Primary Mirror Location". The "Primary Mirror Location" is represented with a dashed line 350 in FIG. 4. A mouse or other pointing device can be used change the location of the mirror via this slider bar. The program could also be modified such that the movement of the primary mirror location 350 could follow the mouse or other pointing device that is moved about the display 400 of FIG. 4. In this implementation the number associated with the location slider bar is in number of pixels. It could also be provided in millimeters or inches. For this particular x-ray there are 5 pixels per mm.

Push button 615 is used to signal the program that the radiologist is done with evaluating this particular x-ray.

Slider bar 620 controls the width (W in FIG. 2) of the ROI. This allows the radiologist to see more or less of the x-ray in the mirrored or replicated displays. For example, it will control the width of the data contained in 220, 320, 920, 930, 940, and 942 as found in the other figures. In this implementation the number associated with the width slider bar is in number of pixels. It could also be provided in millimeters or inches. For this particular x-ray there are 5 pixels per mm.

Slider bar 625 controls the amount of padding (330 and 340) present on either side of the ROI and its copies. In this example the amount of right and left padding is the same. The padding is used to visually separate the mirrored or replicated display from the rest of the x-ray so that the eyes will focus just on the current ROI and its copies. The amount of padding can be reduced to a small number (even zero) to better see the ROI within the context of the x-ray. In this implementation the number associated with the pad slider bar is in number of pixels. It could also be provided in millimeters or inches. For this particular x-ray there are 5 pixels per mm.

Slider bar 630 is used to change the increment of the primary mirror location used by slider bar 610. This affects how many pixels the primary mirror location will change each time either the right or left arrows (i.e., see 526 and 527 of FIG. 5) of slider 610 is clicked. It also sets the increment used when the mirror location is being changed automatically when the "Animate" checkbox 675 is on.

Slider bar 635 contains the number of mirror surfaces (symmetry lines/axes) present in the display. The number of replication surfaces (lines/axes) is the same as the number of mirror surfaces (symmetry lines/axes). Whether or not the data are mirrored or replication is determined by the "Mirror" checkbox 690. If the number of mirrors is set to 0, then just the ROI 220 is display surrounded by the padding width determined by slider bar 625.

Slider bar 640 contains a time delay between display refreshes. The larger the number, the more time the program takes before updating the display. This is only applicable when the "Animate" checkbox 675 is on. On some computers, if the wait value is too small, the display will appear to "flash" because a new image is being displayed before the computer was finished calculating the previous image. On other computers the display many change too quickly and need to be slowed down to grasp the changes.

Figure 11:
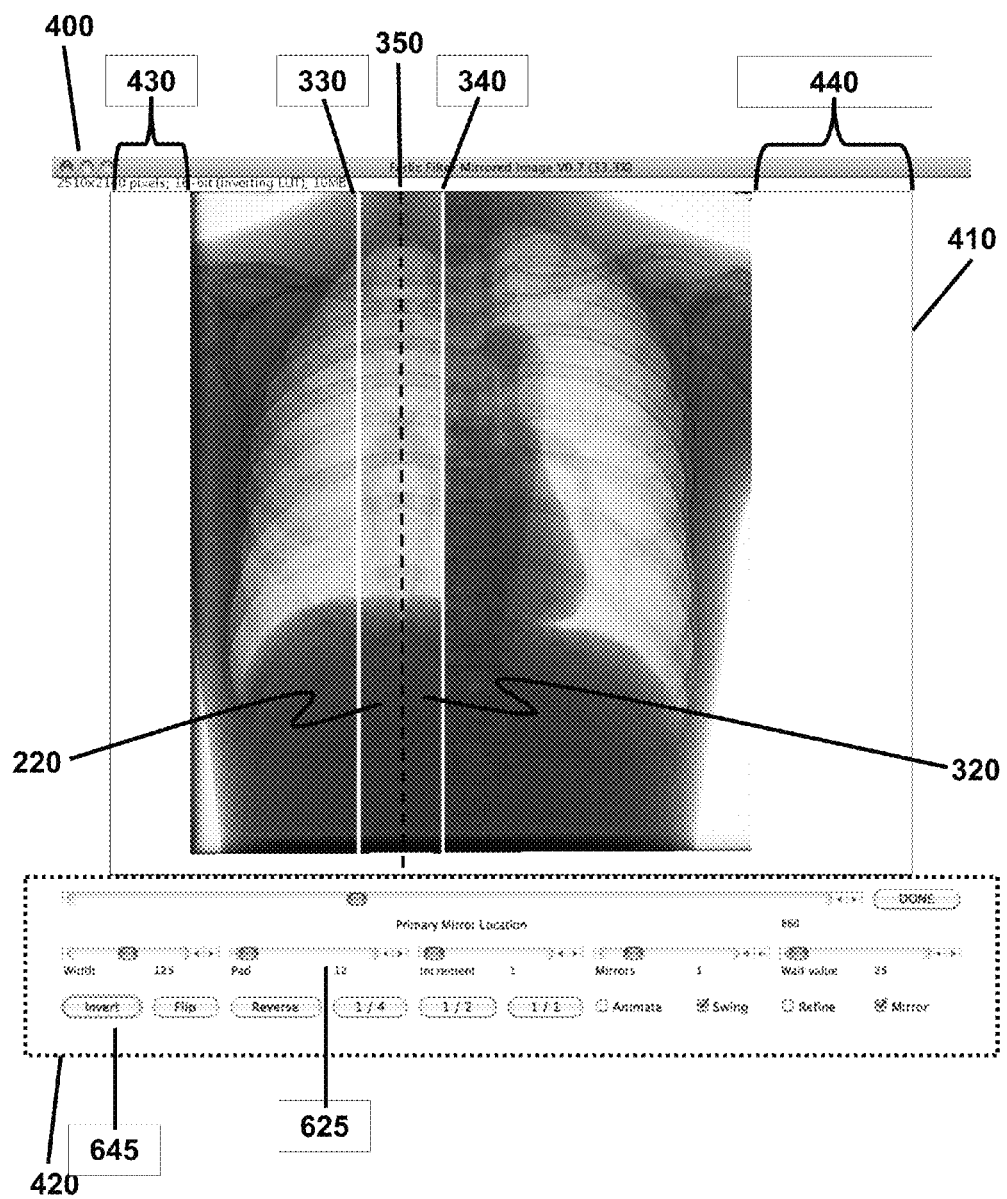
FIG. 11 illustrated inverting the color table used to display the x-ray data.
Figure 12:
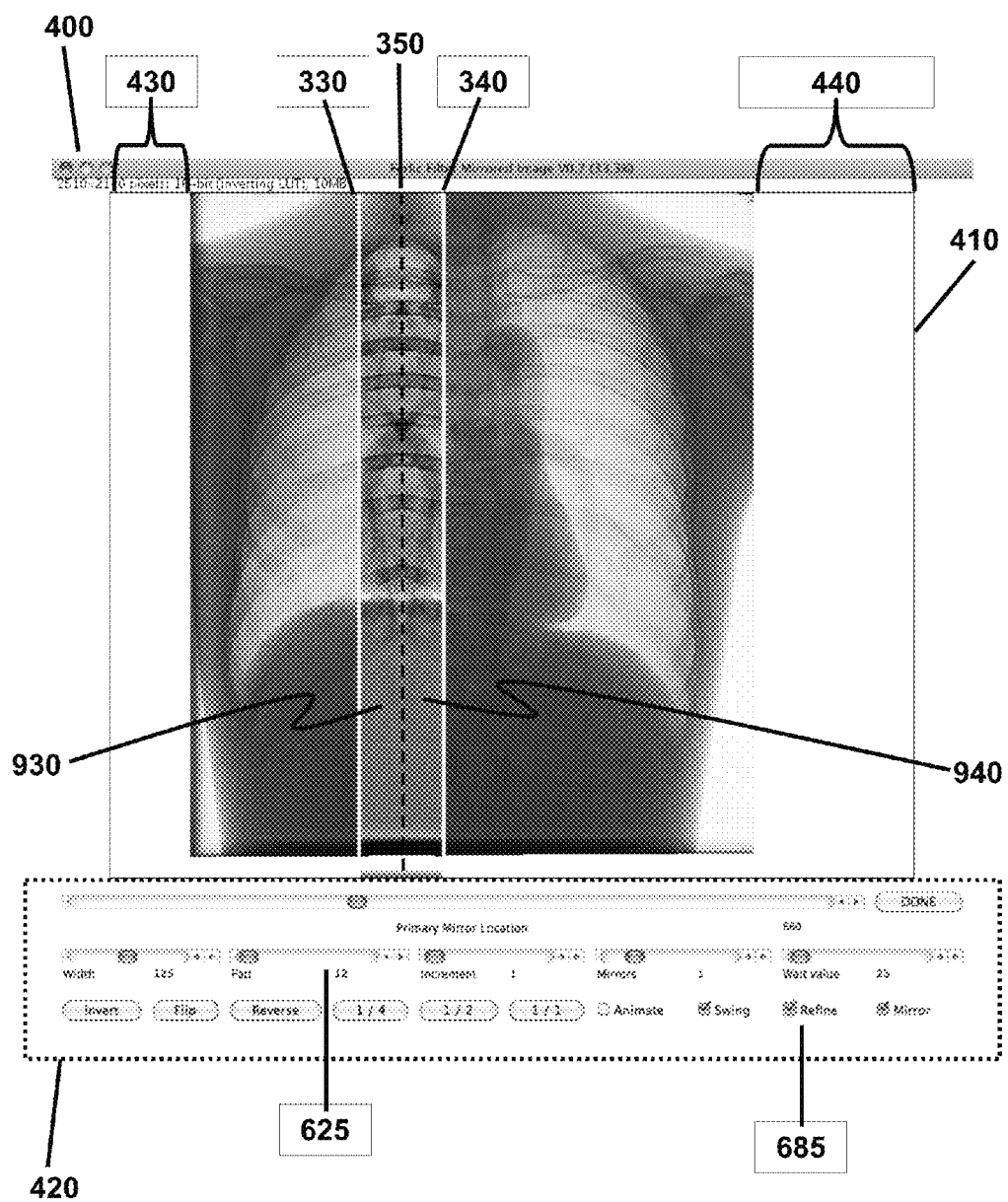
FIG. 12 illustrates using the refine method in conjunction with the inverted color table.
Figure 13:
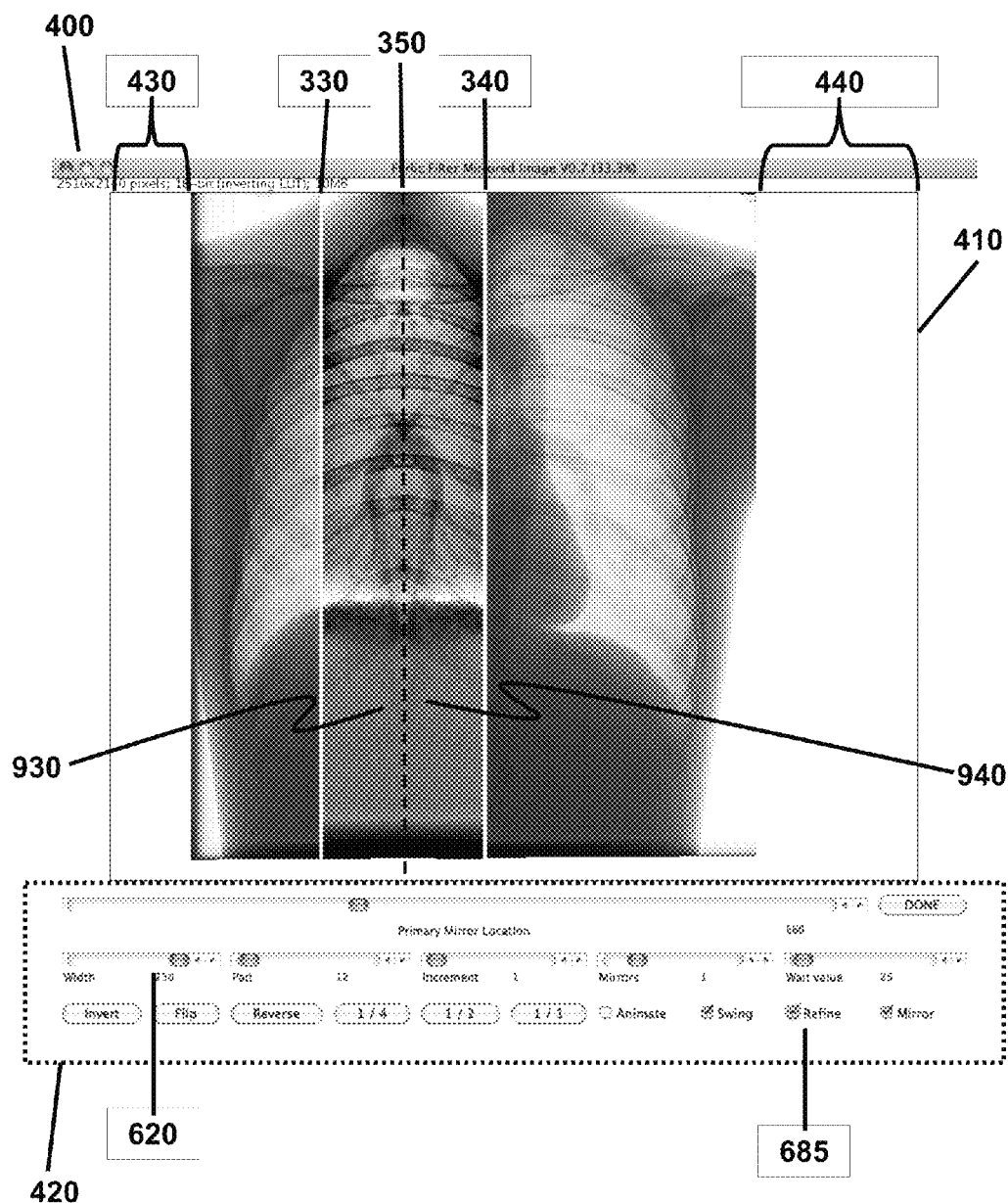
FIG. 13 illustrates changing the size of the region of interest when using the refine option.

Push button 645 "Invert" is used to invert the current color lookup table. FIGS. 11, 12, and 13 provide examples of inverted lookup tables.

Push button 650 "Flip" is used to flip the color of the padding. In this implementation the normal padding is black. Pushing this button once will change it from black to white, or white to black depending upon its current value. Such a change in state could have been accomplished using a check box instead of a push button.

Push button 655 "Reverse" is used to change the direction in which the primary mirror location is moving when the "Animate" check box 675 is on. For example, if it is moving from right to left, pushing this button will reverse the direction to left to right. This button might be used to better understand whether or not an anomaly observed on the x-ray should be classified as a nodule.

Push button 660 "¼" is used to change the value of the increment slider bar 630 to one quarter of the current value of the width slider bar 620. This has application when using the right and left arrows of slider bar 610 to move the mirror (or replicated) display in a slide show type of manner. In this case, each time the mirror is moved, there will be a 75% overlap with the previous display.

Push button 665 "½" is used to change the value of the increment slider bar 630 to one half of the current value of the width slider bar 620. This has application when using the right and left arrows of slider bar 610 to move the mirror (or replicated) display in a slide show type of manner. In this case each time the mirror is moved, there will be a 50% overlap with the previous display.

Push button 670 "1/1" is used to change the value of the increment slider bar 630 to be equal to the current value of the width slider bar 620. This has application when using the right and left arrows of slider bar 610 to move the mirror (or replicated) display in a slide show type of manner. In this case each time the mirror is move, there will be no overlap with the previous display.

Check box 675 "Animate" is used to turn the animation of the primary mirror location on and off. The animation starts up in the direction it was going when it was previously turned off. It will move the mirror location 350 by an amount equal to the current value of the increment slider bar 630. Its action when it reaches one end of the slider bar is determined by the state of the "Swing" check box 680. The "wait value" set with slider 640 determines a relative length of time the program pauses before showing the data from the new mirror location.

Check box 680 "Swing" determines what action is taken when the primary mirror location is incremented past either the right or left end of the slider 610 limits. If the "swing" check box 680 is on, then the motion of the animation will change direction and the slider value will head back in the opposite direction. If the "Swing" check box 680 is off, then when the slider moves past one end of the slider bar, it will jump to the opposite end of the slider bar.

Check box 685 "Refine" is used to provide some type of data refinement to the displayed x-ray in the ROI and its copies. In this example a data amplitude normalization algorithm is used. The algorithm is a type of Automatic Gain Control (AGC) that might be used for seismic data. The Refine button could be used for any number of different data refinement algorithms. This is used just as an example of how modifying the x-ray values can improve the detect ability of nodules, particularly when using the mirrored or replicated display of this invention.

Figure 7:
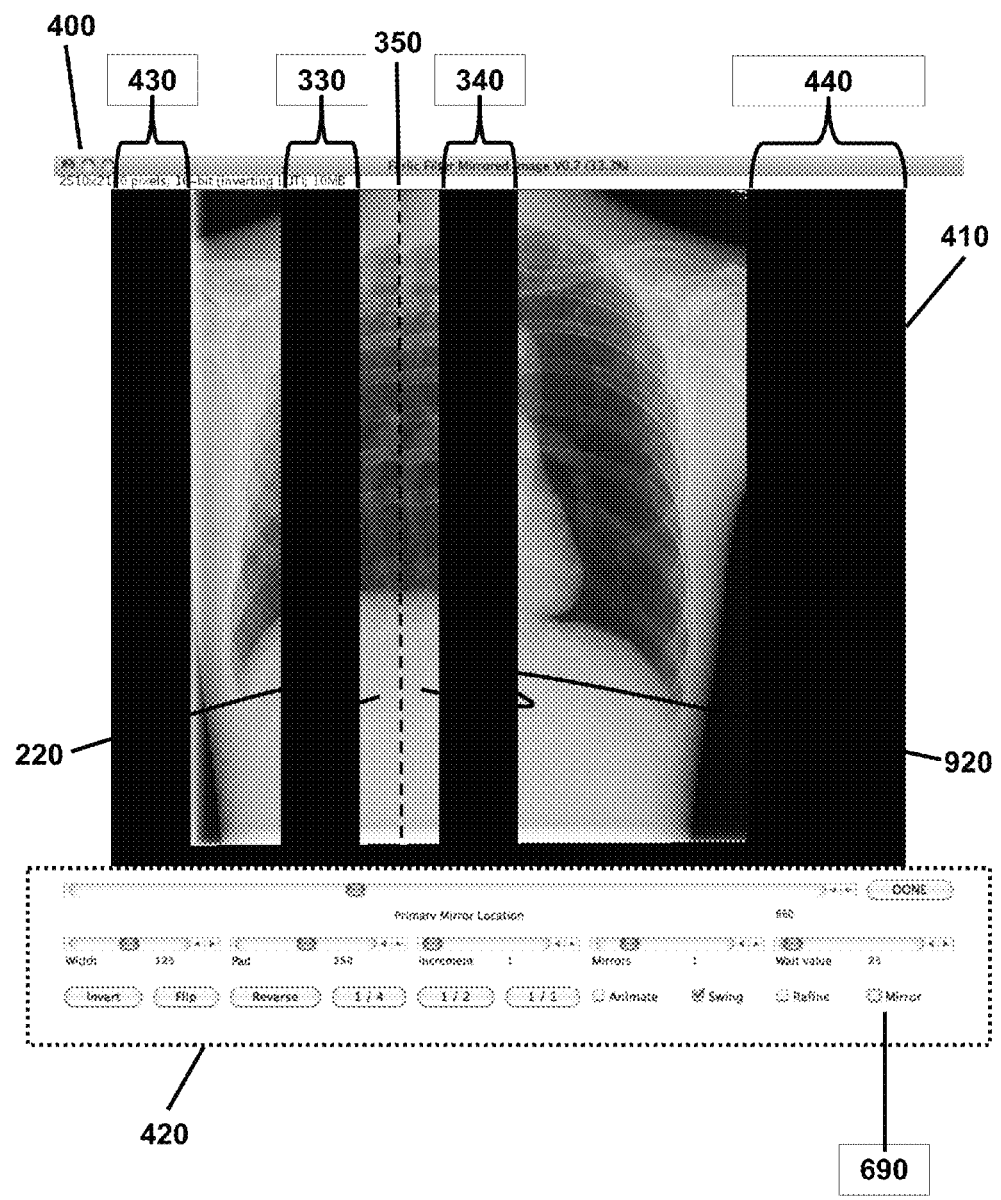
FIG. 7 illustrates a display of the invention using replication instead of mirroring the data in the region of interest.

Check box 690 "Mirror" controls how the data are display across the axis of symmetry 350. If the check box 690 is on, the data are mirrored across the axis of symmetry 350. If it is off, the data are copied. FIG. 7 provides an example display of when check box 690 is off.

FIG. 7 illustrates a display of the invention using replication instead of mirroring of the data in the region of interest. FIG. 4 and FIG. 7 are a comparison of using the symmetry axis 350 to either mirror or replicate the data in the ROI 220. Note that in FIG. 4 there is a smooth data transition across 350 going from the data in 220 to that in 320. In FIG. 7 there is a jump in the data continuity across 350 when going from the data in 220 to that in 920. Turning the mirroring on and off changes the separation of the nodule at the top of the ROI. The nodule is easier to detect in FIG. 4, than in FIG. 7 due to the better symmetry of the displayed data.

Figure 8:
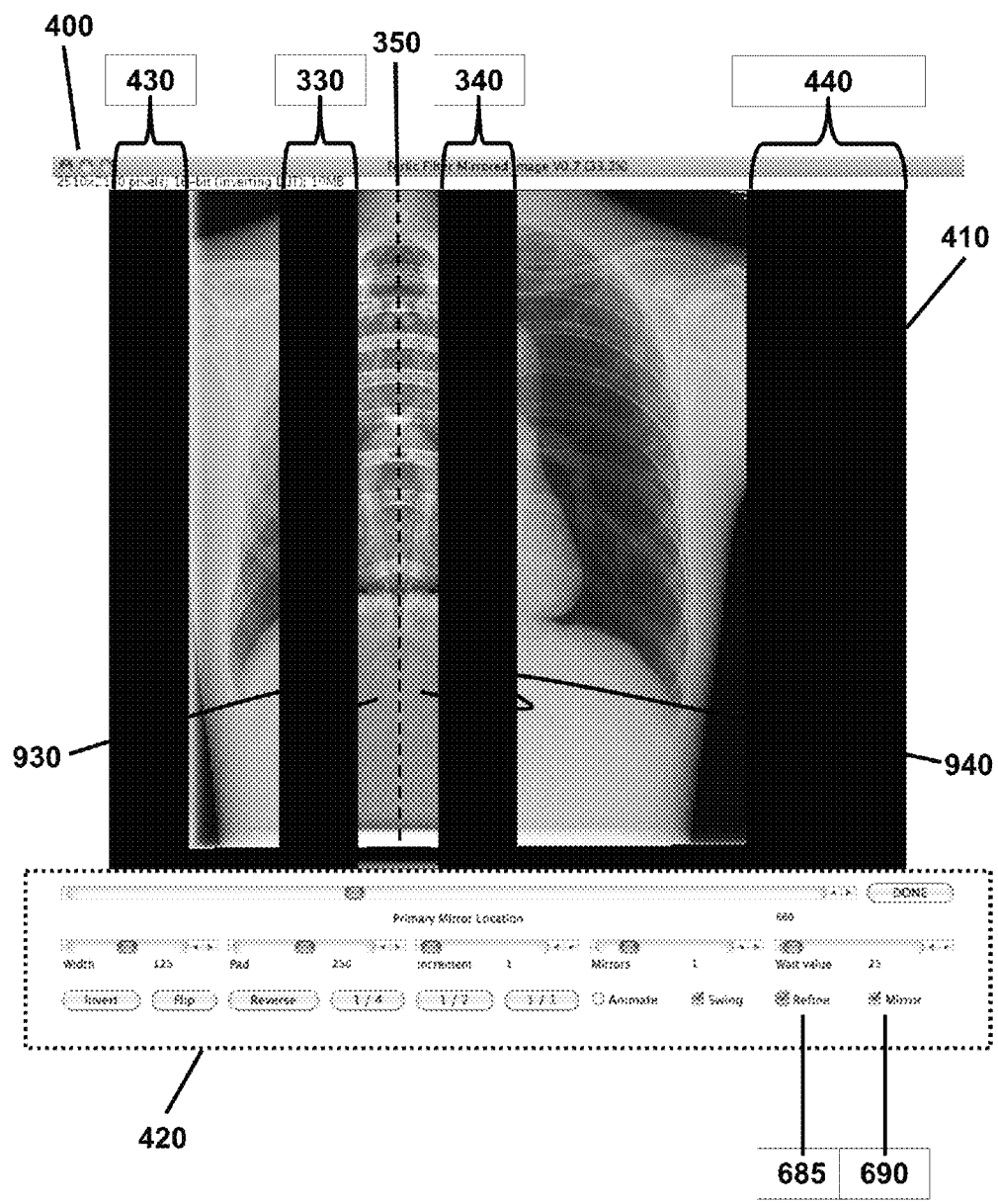
FIG. 8 illustrates using a data refinement method to improve the detect ability of potential nodules.

FIG. 8 illustrates using a data refinement method to improve the detectability of potential nodules. In FIG. 8 the "Refine" check box 685 has been turned on. This converts the FIG. 4 data 220 and 320 to that of 930 and 940 shown in FIG. 8. With this refinement method, the nodules are much easier to detect since they stand out more from the local background values than they do in FIG. 4. This is particularly true when the mirror plane 350 is animated in a movie loop fashion.

Figure 9:
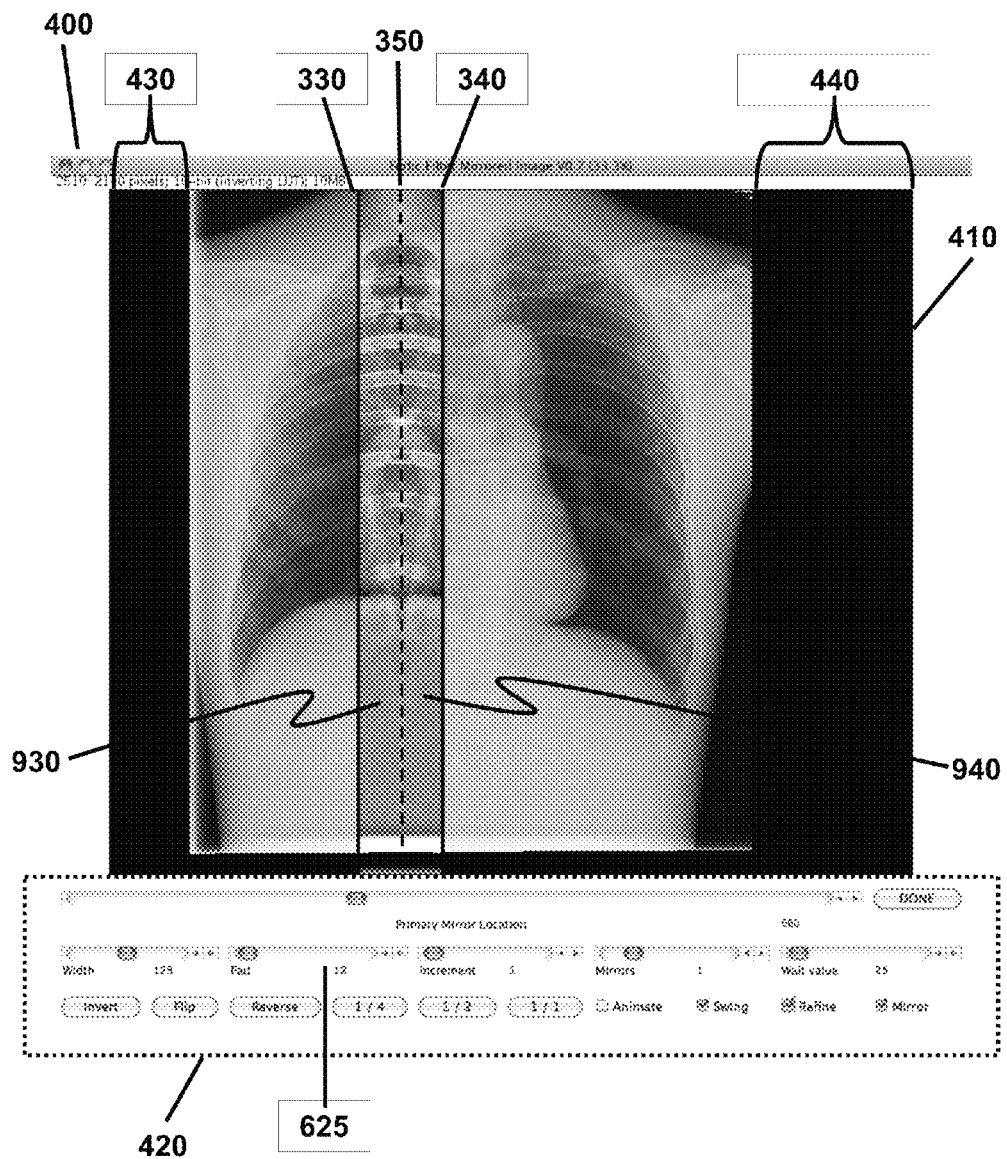
FIG. 9 illustrates changing the padding around the region of interest display.

FIG. 9 illustrates changing the padding around the region of interest display. To generate FIG. 9, the "Pad" slider bar 625 is used to reduce the padding from 250 (in FIG. 8) to 12 (in FIG. 9). All other display parameters are the same between these two figures. Reducing the padding allows the radiologist to view the ROI (930 and 940) in the context of the entire x-ray. Note that 930 is in the proper position, but 940 (mirror image of 930) overlays a portion of the original chest x-ray. If the radiologist wanted to, he/she could have reduced the padding to 0.

Figure 10:
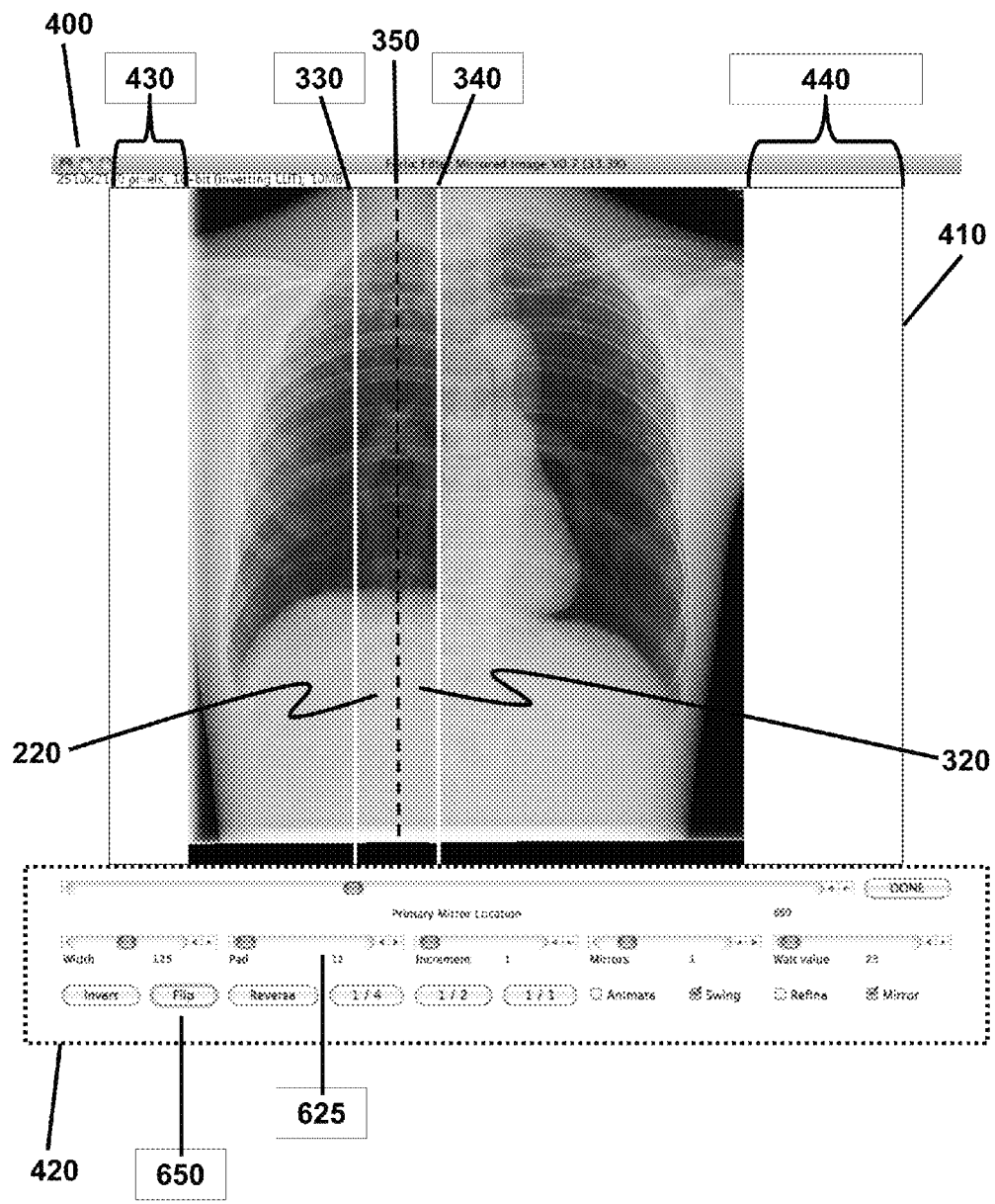
FIG. 10 illustrates changing the color of the padding locations used in the display.

FIG. 10 illustrates changing the color of the padding locations used in the display. FIG. 10 should be compared to FIG. 9. The "flip" button 650 was pushed to flip the color of the padding from black (in FIG. 9) to white (in FIG. 10). In this implementation, the flip button changed the color of the padding found in 430, 330, 340 and 440. The purpose of performing such a change is mainly aesthetics and radiologist preference on whether black, white or some other color helps to distinguish or isolate the ROI 220 and 320 from the rest of the x-ray. A program to implement the invention does not need to have the ability to change the color of the padding, but having such an option should improve the usability of the invention.

FIG. 11 illustrates inverting the color table used to display the x-ray data. FIG. 11 should be compared to FIG. 10. The "Invert" button 645 was pushed to invert the grey scale of the x-ray within the image 410. Note that in this implementation, inverting the color scale does not change the padding color. It is still white. In this inverted color scale the nodules will be darker than their surroundings instead of lighter as in the previous figures. Which color look-up table to use is a matter of the radiologist's personal preference. A program to implement the invention does not need to have the ability to change the x-ray color scale, but having such an option should improve the usability of the invention.

FIG. 12 illustrates using the refine method in conjunction with the inverted color table. FIG. 12 should be compared with FIG. 11. The difference between these two figures is that the "Refine" option 685 has been turned on in FIG. 12 and not in FIG. 11. In this figure the nodules will be darker than their surroundings. The nodule towards the top of the ROI (as denoted with 360 in FIG. 3 and FIG. 4) is easier to see in FIG. 12 than in FIG. 11.

FIG. 13 illustrates changing the size of the region of interest when using the refine option. In FIG. 13, the width of the ROI 930 and its mirror image 940 has been changed from 125 in FIGS. 12 to 250 in FIG. 13. With this increased ROI size the nodule is a little more apparent. The geometric patterns of the ribs and bronchioles are very different from that of the single nodule.

Figure 14:
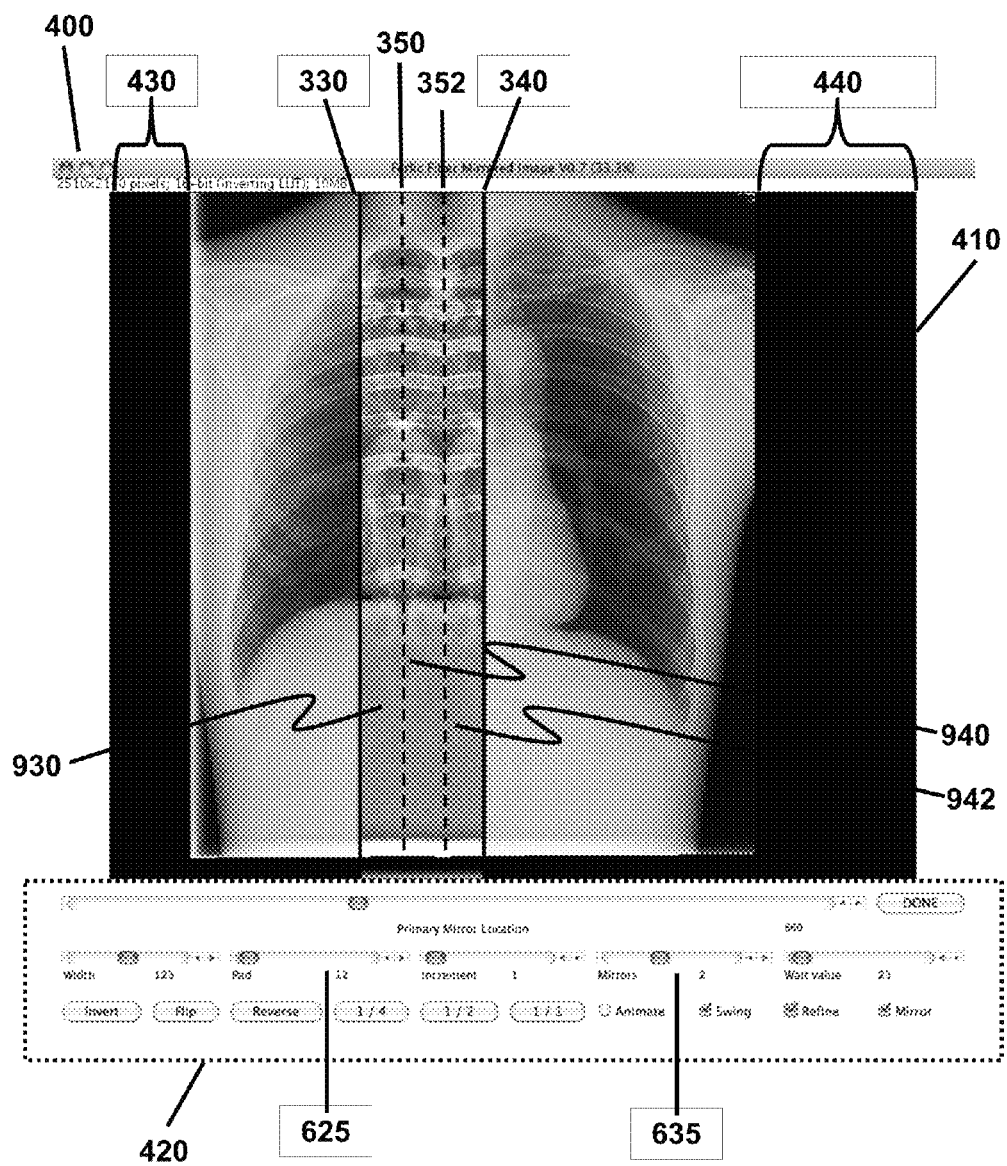

FIG. 14 illustrates using two mirror surfaces with refine on. FIG. 14 is a change relative to FIG. 9, in which the mirror slider bar 635 is used to increase the number of mirrors from 1 to 2. This adds the display region 942 to the overall Region of Interest ROI display. A new mirror surface (otherwise called an axis of symmetry) 352 is inherent in the display. The dashed line 352 shows the location of this new mirror surface, but in normal use of the invention the dashed line would not be displayed. An arbitrary number of mirrors can be utilized in the invention. Using an odd number of mirrors generally works better than using an even number of mirrors. With an odd number of mirrors, if nodules are present, they will always appear in pairs.

Figure 15:
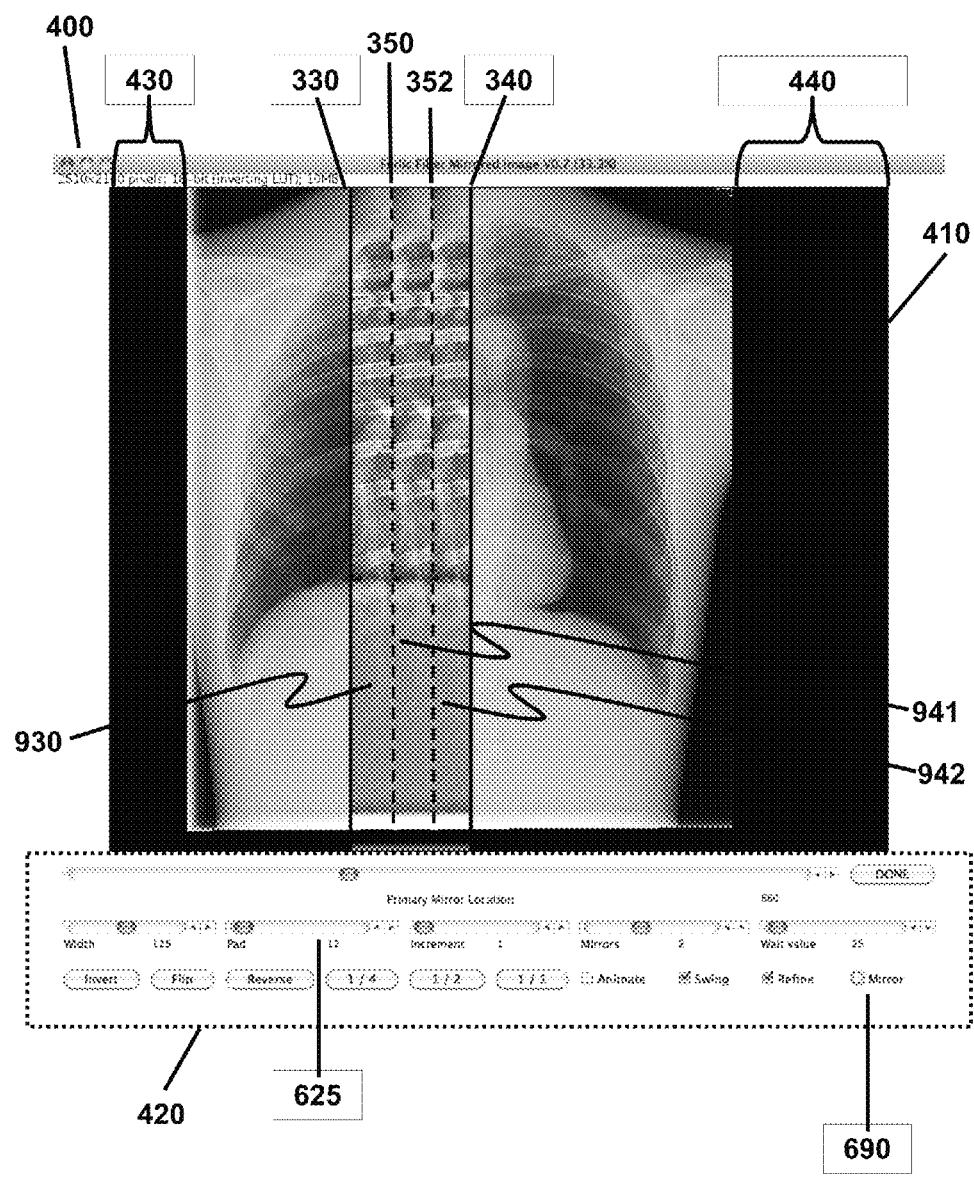

FIG. 15 illustrates using two replication surfaces with refine on. FIG. 15 is a change relative to FIG. 14 where the mirror check box 690 has been turned off. This causes the region marked 940 in FIG. 14 to become 941 in FIG. 15. Note that in FIGS. 15 930, 941, and 942 look the same, except they are displaced relative to each other. The x-ray data across the replication axes 350 and 352 is no longer smooth, but shows discontinuities. Some radiologist may find the movement of the replication mirror plane across the x-ray to provide a better means of identifying nodules, but it is expected that most radiologist will prefer using the mirror planes, with refine on.

Figure 16:
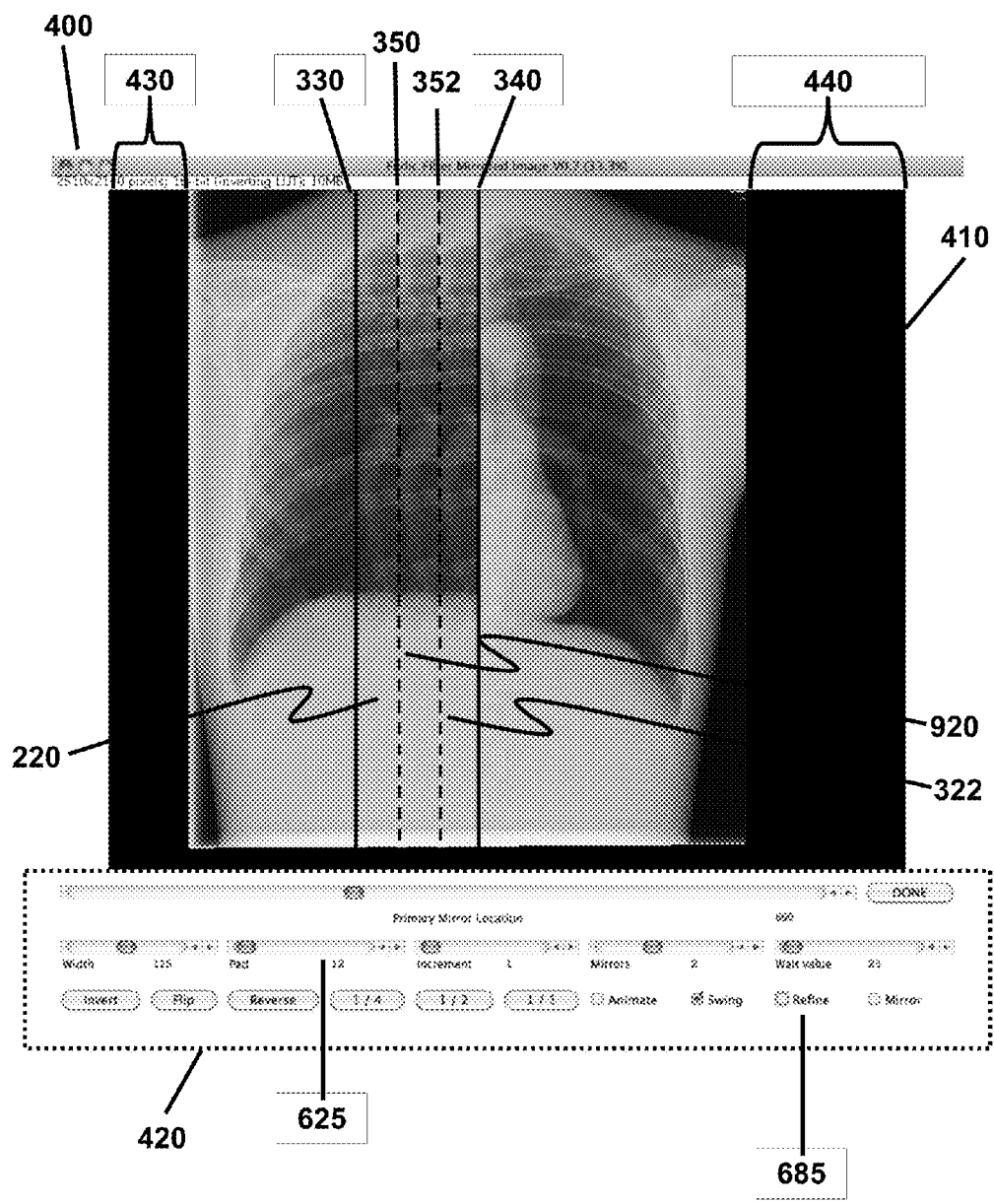
FIG. 16 illustrates using two replication surfaces with refine off.

FIG. 16 illustrates using two replication surfaces with refine off. FIG. 16 is a change relative to FIG. 15, where the refine checkbox 685 is turned off. Most will find the nodule is a little harder to see in FIG. 16 than it is in FIG. 15. This figure further illustrates the importance of using data refinement methods, in conjunction with the invention, to better identify potential cancerous nodules.

Figure 17:
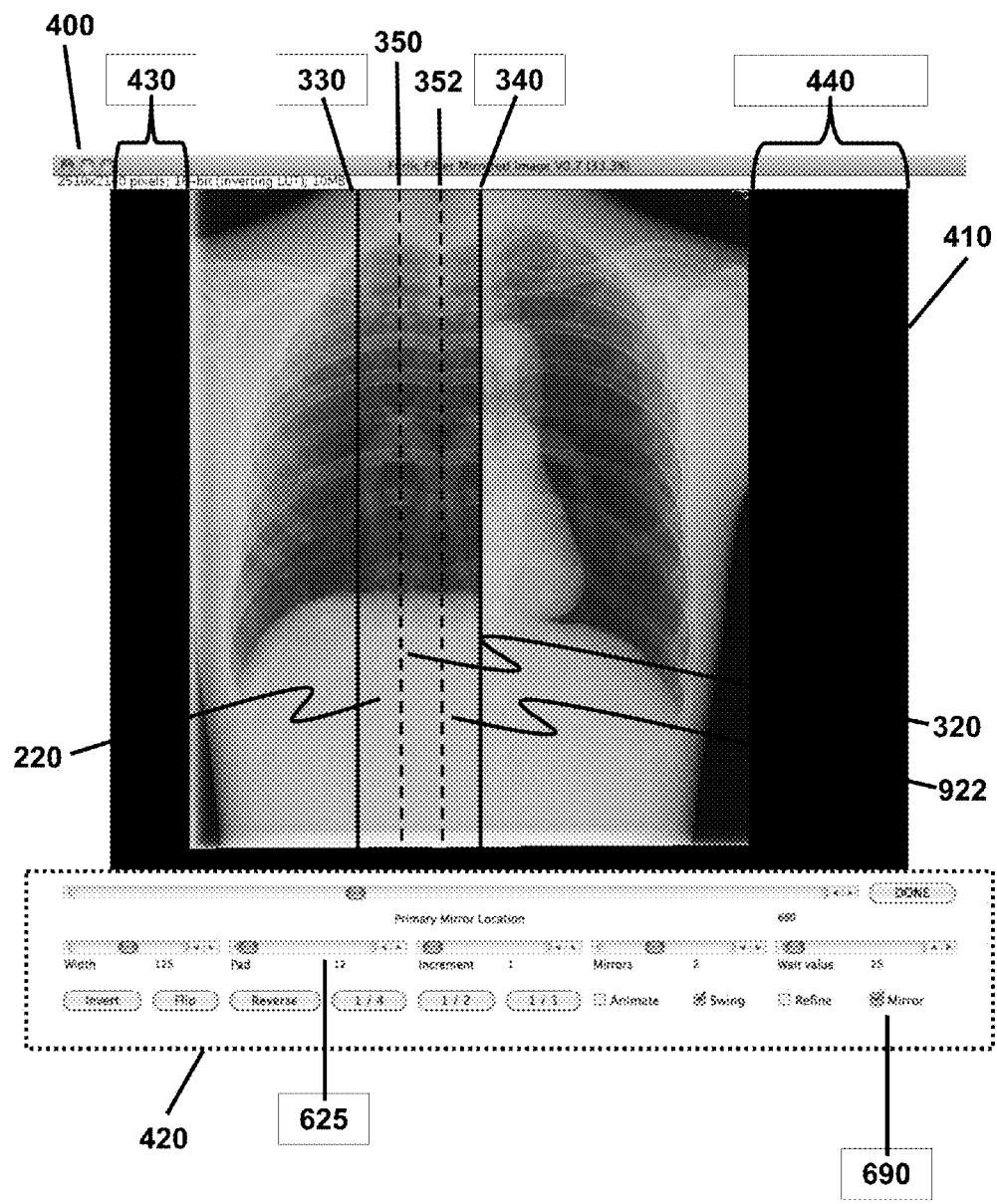
FIG. 17 illustrates using two mirror surfaces with refine off.

FIG. 17 illustrates using two mirror surfaces with refine off. FIG. 17 is a change relative to FIG. 16, where the mirror checkbox 690 is turned back on. This has the affect of reversing the direction in which the data are displayed in 920 of FIG. 16 to produce 320 in FIG. 17. The data transitions smoothly across the lines of symmetry 350 and 352 in FIG. 17, instead of having discontinuities across these lines in FIG. 16. Most will find the nodule easier to see in FIG. 17 than FIG. 16.

Figure 18:
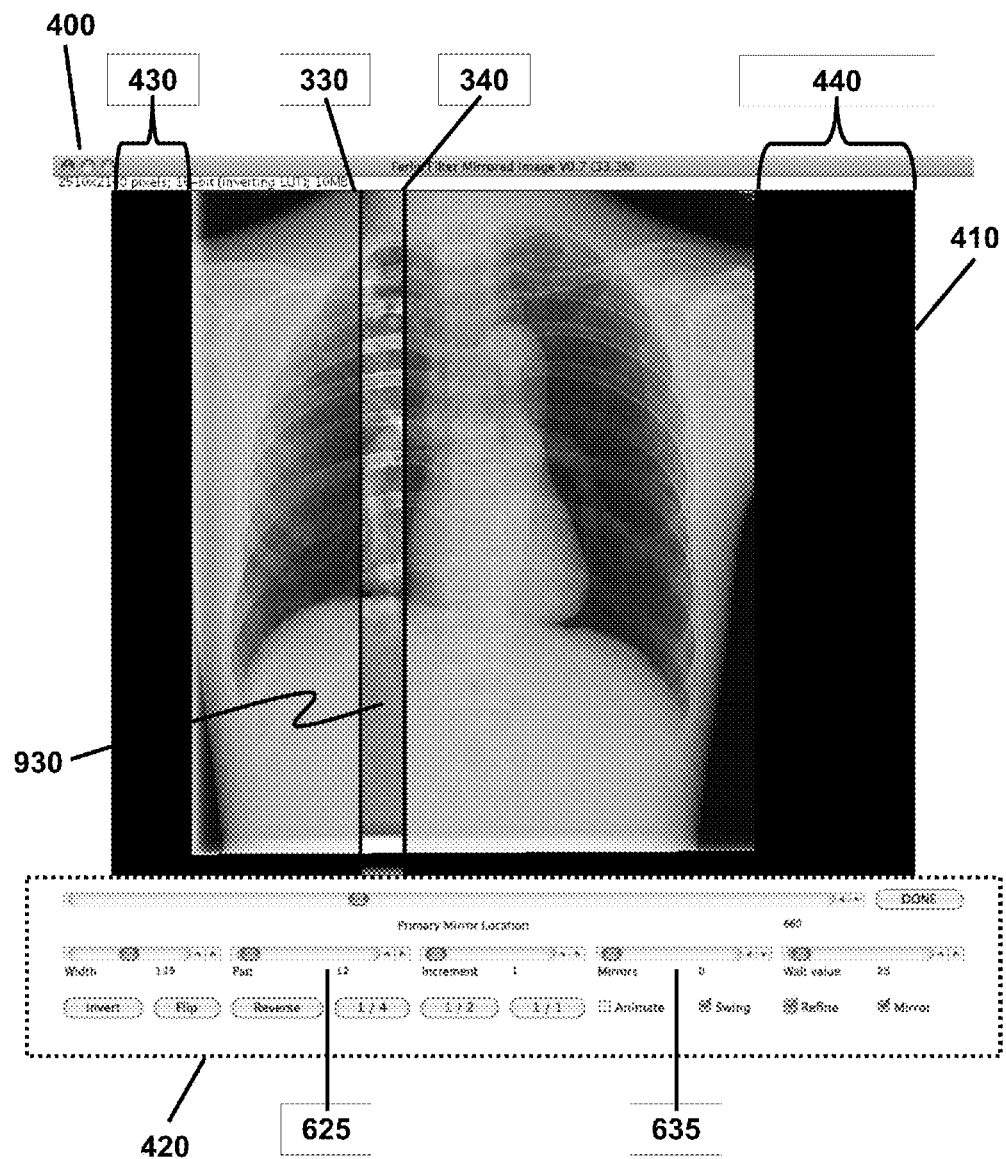
FIG. 18 illustrates displaying just the region of interest with refine on and no mirror or replication surfaces.

FIG. 18 illustrates displaying just the region of interest with refine on and no mirror or replication surfaces. FIG. 18 is a change relative to FIG. 9, where the number of mirrors slider bar 635 is changed from 1 in 0. In FIG. 18, just the ROI 930 is displayed using the data refinement method. This feature of removing the mirrored or replicated data is useful if the radiologist wants to see just the ROI 930 in its context of the chest x-ray 410. This can allow the radiologist to better insure he/she does not identify a false positive nodule. In this figure the padding width 625 is small enough to clearly identify the ROI 930 without covering much of the background x-ray.

Figure 19:
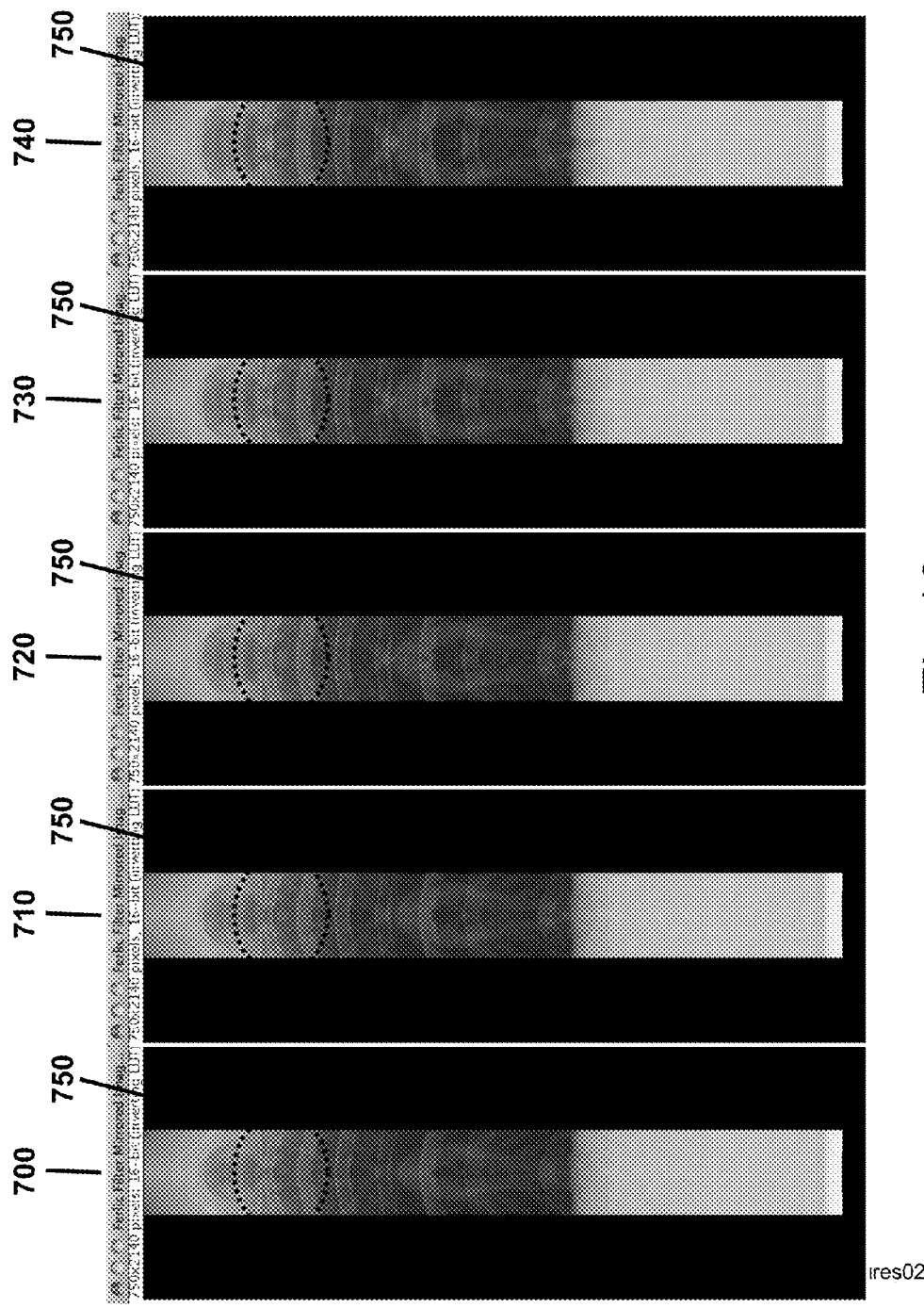

FIG. 19 illustrates moving the mirror surface across the x-ray without the refine option being on. FIG. 19 contains a sequence of five screen captures of the invention embodiment shown previously in FIG. 3. In FIGS. 19, 700, 710, 720, 730, and 740 represent the display when the ROI (220 of FIG. 2) is moved in steps across the x-ray 110 of FIG. 2. A particular area of this display is noted with 750 to observe what happens when the mirror surface encounters a nodule.

In viewing these images sequentially from left to right, the nodule looks like it is undergoing "cell division". If viewed sequentially from right to left it would look like "cell collision".

In 700 the axis of symmetry (350 of FIG. 3) is just on top of the left edge of the nodule. In 710, the axis is about in the middle of the nodule, and it appears as if there is one entire nodule in the display, whereas what we are really seeing is only the left half of the nodule and its mirror image. In 720 the mirror surface has moved close to the right edge of the nodule. This image has the appearance of a cell just about to complete cell division. In 730 the mirror surface is just to the right of the nodule, and in 750 it is a little ways past the right side of the nodule.

When shown in a movie loop, with a much finer movement of 350, it will look like the nodule grows from the center of the display to a single nodule, this nodule will then split into two (like a cell dividing), and then the two nodules will separate from each other and move further and further apart along a horizontal line until they leave the display. Only features in the x-ray that are circular will exhibit this type of apparent "cell division" motion. Non-nodule feature will have a vertical component to their apparent motion, so they will appear to either fall down from, or climb up from the mirror surface. When the ROI moves from right to left, the sequence of images will be reversed. In this case the two nodules will come together along a horizontal line, collapse into one, and then disappear. This type of motion might be called "cell collision" or "cell fusion".

Figure 20:
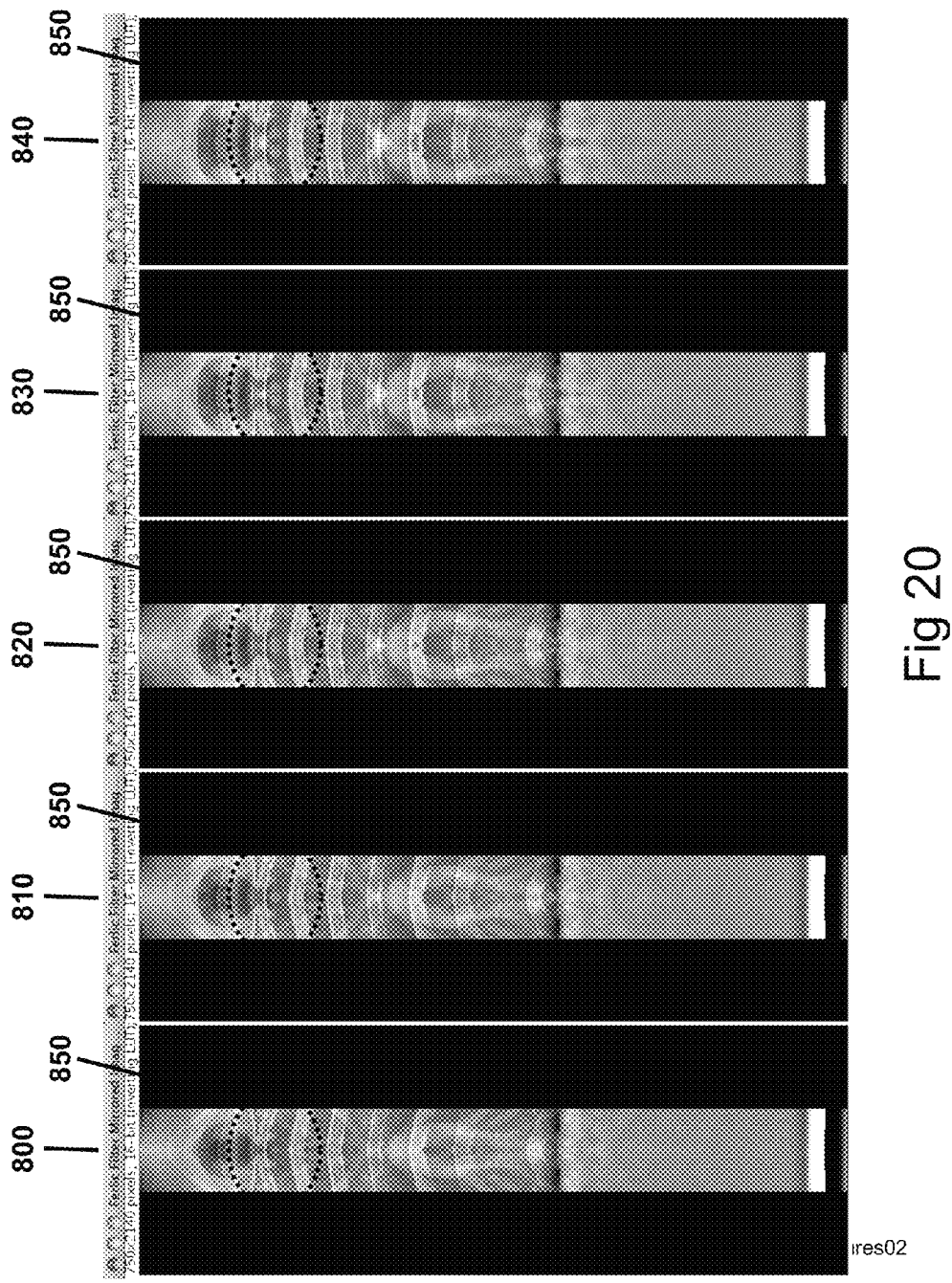

FIG. 20 illustrates moving the mirror surface across the x-ray with the refine option being on. This is a similar set of screen captures as shown in FIG. 19, with the exception that the data displayed have had the refine method applied to them before being displayed. This particular refinement method improves the detectability of the nodule contained in the oval marked as 850.

FIG. 20 contains a sequence of five screen captures of the invention embodiment shown previously in FIG. 3. In FIGS. 20, 800, 810, 820, 830, and 840 represent the display when the ROI (220 of FIG. 2) is moved in steps across the x-ray 110 of FIG. 2. A particular area of this display is noted with 850 to observe what happens when the mirror surface encounters a nodule.

In viewing these images sequentially from left to right, the nodule looks like it is undergoing "cell division". If viewed sequentially from right to left it would look like "cell collision".

In 800 the axis of symmetry (350 of FIG. 3) is just on top of the left edge of the nodule. In 810, the axis is about in the middle of the nodule, and it appears as if there is one entire nodule in the display, whereas what we are really seeing is only the left half of the nodule and its mirror image. In 820 the mirror surface has moved close to the right edge of the nodule. This image has the appearance of a cell just about to complete cell division. In 830 the mirror surface is just to the right of the nodule, and in 850 it is a little ways past the right side of the nodule.

When shown in a movie loop, with a much finer movement of 350, it will look like the nodule grows from the center of the display to a single nodule, this nodule will then split into two (like a cell dividing), and then the two nodules will separate from each other and move further and further apart along a horizontal line until they leave the display. Only features in the x-ray that are circular will exhibit this type of apparent "cell division" motion. Non-nodule feature will have a vertical component to their apparent motion, so they will appear to either fall down from, or climb up from the mirror surface. When the ROI moves from right to left, the sequence of images will be reversed. In this case the two nodules will come together along a horizontal line, collapse into one, and then disappear. This type of motion might be called "cell collision" or "cell fusion".

Figure 21:
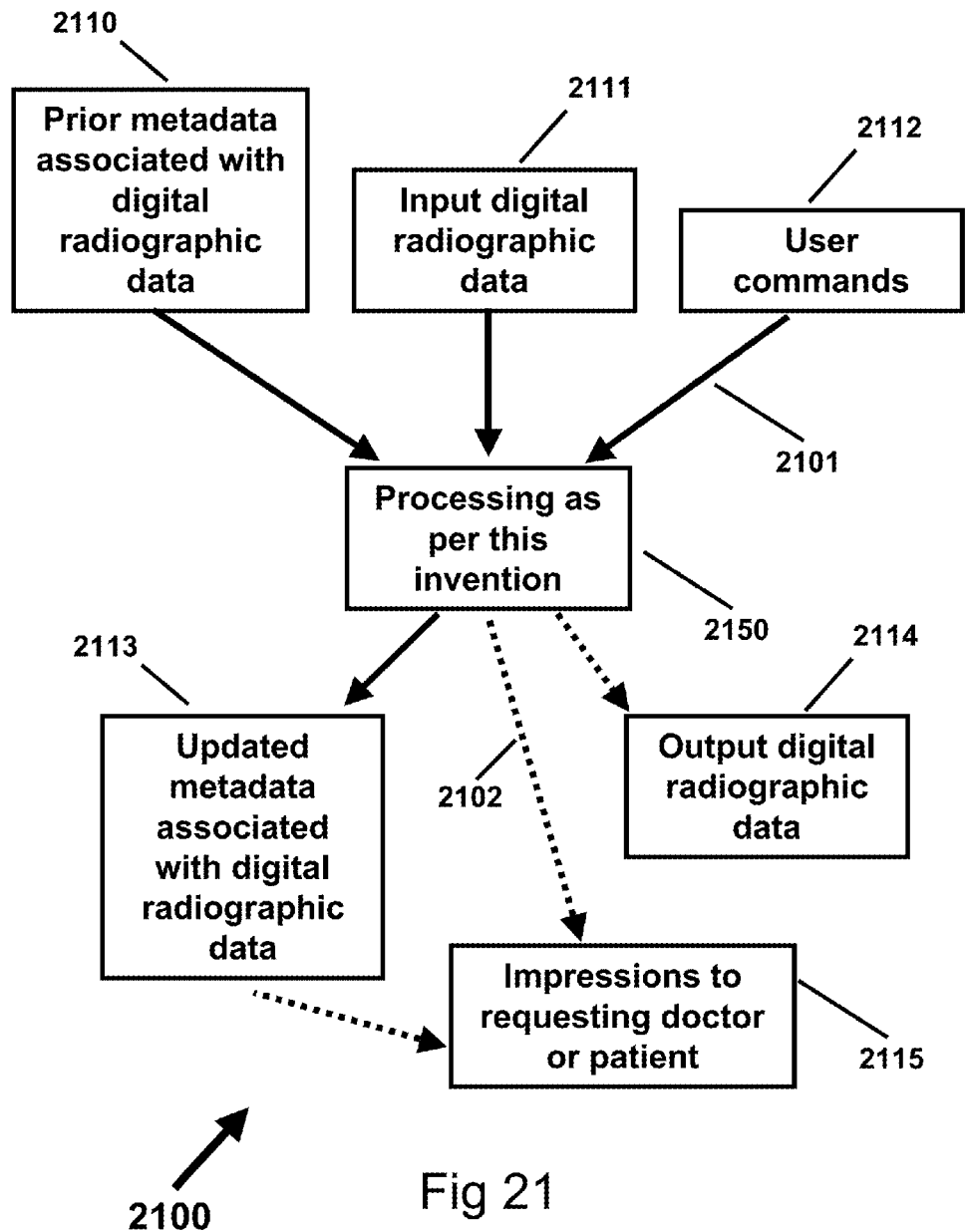
FIG. 21 illustrates how this invention might fit into the workflow or data stream of a conventional digital radiograph interpretation.

FIG. 21 illustrates the main components of a system, 2100, that might be used to implement this invention. In this figure the solid lines with arrows (for example 2101) indicate the primary flow of information or data. The dashed lines with arrows (for example 2102) indicate the potential flow of information or data.

The center of FIG. 21, 2150, is the processing of the data as per this invention. This box will be explained in more detail with FIG. 22.

There are three inputs into 2150. Item 2110 represents the prior metadata associated with the digital radiographic data that comes from 2111. In some systems these two pieces of information may come from the same source, or they could come from different sources. The prior metadata consists of such things as the patient's name, information concerning how the radiographic data were collected, the format the data is store in, prior interpretations or readings of the data, and other types of metadata that are currently, or might be in the future, associated with the digital radiographic data or the patient. Item 2111 represents the actual digital radiographic data that will be used by the invention. This data might be in a DICOM, RAW, or some other data format that is, or later becomes, standard practice for digital radiographic data storage. This information may come directly from the x-ray machine, an external storage device such as a CDROM or thumbdrive, via the internet, an intranet, or other types of digital data storage devices. This information may be stored in PACS (picture archiving and communication system), RIS (radiology information), CVIS (cardiovascular imaging systems), or other such systems that are, or may in the future, be used to store and organize radiographic data and its associated metadata. Also feeding into 2150 are user commands, 2112, that provide instructions on how the invention is to be utilized. The methods in which these data are fed into 2150 will be discussed more in FIG. 22.

There are three possible outputs from 2150. These are updated metadata associated with the digital radiographic data (2113). For the most part this will be the location of nodules identified by this invention, the radiologist's comments concerning the nodules or other aspects of the x-ray, along with other information such as the time, date, location and doctor's name who performed the diagnosis. Display settings used in the invention to obtain the results might also be stored. The radiologist might also decide to keep a copy of any modified radiographic data, such as that produced by the refine method (e.g. 685 of FIG. 8) that is applied to all or a portion of the digital radiograph. The radiologist might also want to generate and save movie loops that illustrate a particular feature. These might be stored as radiographic data (2114) or metadata (2113).

The pertinent parts of the radiologist's findings needs to be transmitted to the requesting doctor and/or to the patient directly. This is done in item 2115. Normally these findings would be placed in the metadata repository, such as a PACS system, and the doctor would access such a system to obtain the radiologist's findings. However, there may be times in which pertinent findings need to be transmitted to the doctor and/or patient without delay. Therefore the process should have an avenue of doing this. It could be performed via an email message, text message, or voice message to the appropriate recipient.

Figure 22:
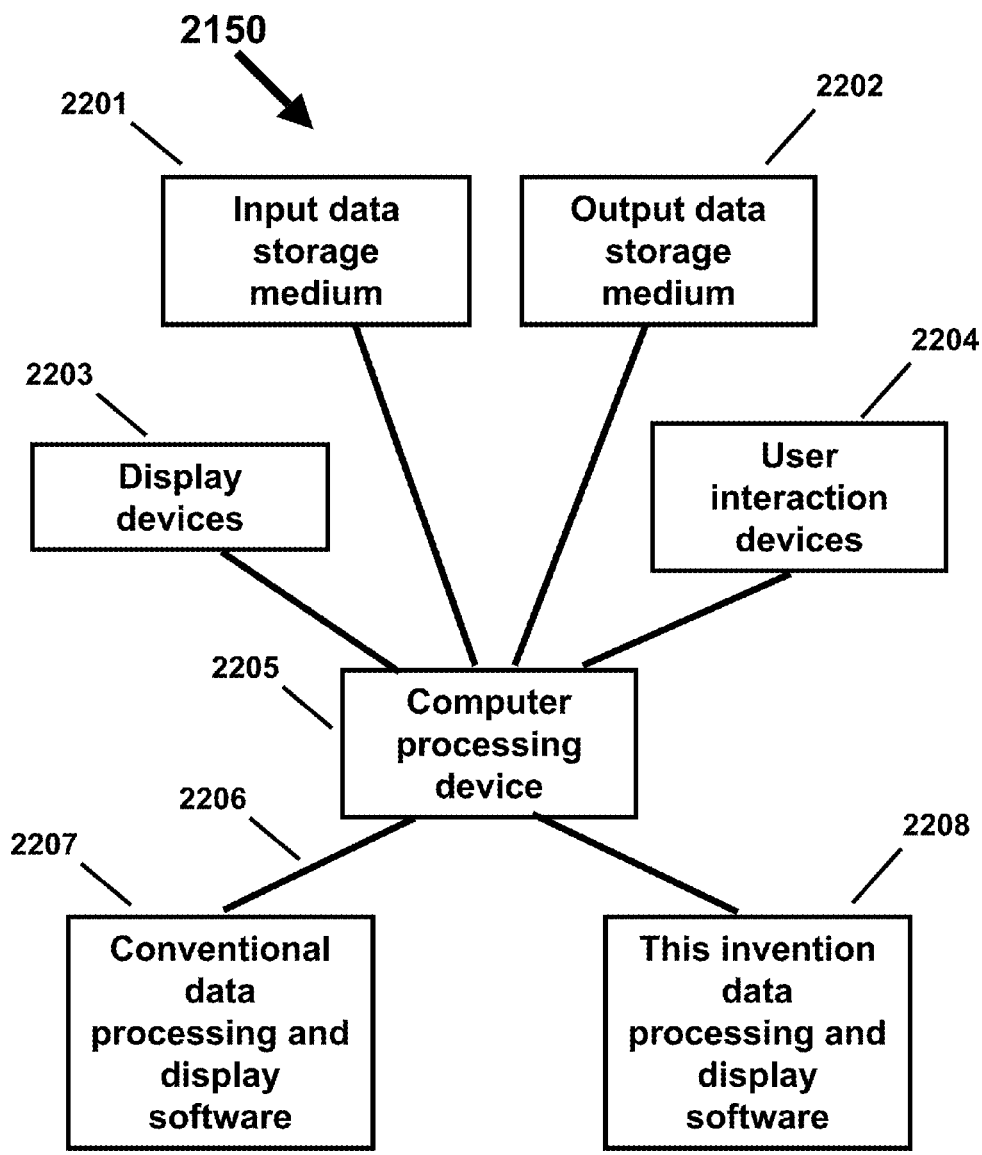
FIG. 22 illustrates the various computer components that this invention might utilize.

FIG. 22 provides an example of a processing system (2150) used to implement this invention. In this figure the solid black lines, such as 2206, indicate how the devices could be connected. These connections may be a physical wire, or part of the same physical device, being on the same circuit board, or chip. They could also occur wirelessly. Each of the individual items in this figure could be combined with other items in the same physical container, or they may be separate. Not all of the items have to be present. Other items could be connected that are now, or might be in the future, used with a computer processing device.

Such a system (2150) would have means of retrieving input data (2201) from some form of storage device. This might be a physical device such as a disk drive hooked directly to the computer processing device (2205), an external storage media and media reader such as a CDROM and CDROM reader, or some storage accessed via the internet, local area network, Bluetooth, etc. This device is where the input data (2110 and 2111 of FIG. 21) most likely would come from. The user commands, 2112 FIG. 21, might also come from such devices, but not normally.

The system also needs some form of output storage device, 2202. This could be the same or similar device as those used for input (2201).

The system will also need some form of display device (2203). This could be any type of display device, some example of which are: computer monitor, a video projection system, a tablet, or touch screen device. Hard copy devices such as printers, plotters, and cameras could also be used to display the results of this invention. Any device currently used, or that is used in the future, to view the results of a computer could be used as the display device, 2203. There might be more than one device. The computer might display the same information on each of the multiple devices, or different information on different devices.

The user will need to interact with the computer through some form of user interaction device, 2204. This is predominantly where the user commands, 2112 of FIG. 21, will be obtained. A keyboard and mouse are common types of interaction devices. However a touch sensitive screen and finger, some form of motion tracking, eye tracking or voice recognition device might also be used. Any currently used device, or devices used in the future, to provide input to a computer type of device (2205) could be used as the user interaction devices (2204). There may be one or multiple such devices.

The computer processing device, 2205, is at the center of this system. This might be a standard computer, a graphics computer, GPU, some type of computing tablet, an iPad, a parallel computer, or some form of cloud computing. The computer processing device would need to contain memory, some form of operating system, a means of communicating with the other devices, and to run or execute the data processing and display software written for this invention (2208). It would also benefit greatly from running conventional data processing and display software (2207). Devices needed for 2205 are well known by the industry.

The system 2150 could be made of a different physical device for each of the elements of FIG. 22, devices that have several of the devices shown in FIG. 22 combined into one device, or something that contains all of the devices shown in FIG. 22 in one physical device. For instance, a laptop computer could be used to house all of the elements of FIG. 22 into one physical device.

Item 2208 refers to the software written to implement this invention. Using the description provided above, an individual skilled in computer programming should be able to easily implement this invention using computer languages such a C, C++, Java, and other know computer languages, and those that might be available in the future.

Item 2207 refers to software currently utilized by radiologist to view and interpret radiographic data. The "iNtution" software from TeraRecon is one such software package that might be used by a radiologist to study chest x-rays to identify lung nodules. Another package might be OsiriX, an open-source PACS workstation DICOM viewer (www.osirix-viewer.com).

The radiologist will use the User interaction devices (2204) to instruct the program (2208) which options to implement. As the radiologist scans a radiograph with this invention, the radiologist will identify nodules based on the radiologist's knowledge of the human anatomy and the type of radiograph the radiologist is viewing. The invention will help make such nodules easier to identify. Once a nodule, or potential nodule is identified, the radiologist will use the User interaction device, (2204) to instruct the program (2208) to record the location of the nodule (along with any comments the radiologist might want to make concerning the nodule). Such records can then be stored to the Output data storage medium (2202). The radiologist will then continue to scan the radiograph until the radiologist is no longer able to identify additional nodules. In performing such viewing, the radiologist might want to also view or manipulate the radiograph using conventional data software (2207). Or the invention might be licensed to makers of conventional data processing software (2207) such that the invention software (2208) becomes a part of the conventional software package (2207).

One useful form of modifying the input data to improve the ability to detect nodules is to apply a gain function that has the form of equation 1 below. The variables A, B, and C can be set to produce a variety of amplitude changes, such as those that are known in the industry, for example a conventional (AGC). It can also produce new gain effects, such as the Refine Gain, and Remap Gain methods described below. These new gain methods can help enhance the anomalous x-ray values that may be indicative of nodules. This type of modification changes the values of that data that are displayed through the display color lookup table, therefore a test needs to be made that the output value calculate does not exceed either the minimum or maximum allowed value. If it does then it should be set to the appropriate minimum or maximum value it exceeds.

$$\text{output}=(\text{input}-A)*B+C \tag{1}$$

where:
- output=changed value of an input pixel in the modified image,
- input=original value of the corresponding input pixel in the input image,
- A=a user defined constant, possibly in combination with a value derived from the pixel values in a window around the input point,
- B=a user defined constant possibly in combination with a value derived from the pixel values in a region around the input point,
- C=a user defined constant possibly in combination with a value derived from the pixel values in a region around the input point, No Gain Application:
Equation 1 can be used to leave the input data unchanged by using:
- A=0,
- B=1, and
- C=0.

Conventional AGC:
To reproduce a conventional AGC routine,
- A=either zero, the mean or the median of the input image,
- B=scalar/(local mean), and
- C=A, where the scalar could be the mean or median value of the amplitude range used for the display's color lookup table, and the local mean is calculated from a region around the input data point.

There are several ways to calculate the local mean.
1) calculate either the mean or median of all the pixels located in a box that is centered on the input point. The size of the box can be proportional to the width of the strip that is being mirrored.
2) similar as 1) above, but use the same local mean value for all pixels on the same row when using a vertical strip, or the same column when using a horizontal strip.

Refine Gain Method
This method in current studies provides better visual discrimination of nodules than the conventional AGC gain method. For this gain method,
- A=local mean,
- B=constant gain value (for example 2.5),
- C=constant gain value (for example 0.9) multiplied by regional mean (e.g. entire image)

Remap Gain Method
- A=Lmin,
- B=(Gmax−Gmin)/(Lmax−Lmin)
- C=Gmin

Where:
- Lmin=local minimum value around input pixel
- Lmax=local maximum value around input pixel
- Gmin=global minimum value (from entire or large portion of image)
- Gmax=global maximum value (from entire or large portion of image)

In implementing this gain function, the region around the input pixel could have an area equal to the square of the width of the smallest dimension of the region of interest.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method for detection of nodules in a medical image, the method comprising:
   (a) receiving, by a computer processing device, image data representing the medical image;
   (b) receiving, by the computer processing device, a selection of a region of interest in the medical image;
   (c) copying, by the computer processing device, the image data contained within boundaries of the region of interest;
   (d) outputting for display, by the computer processing device, an output image containing a first copy of the image data contained within the boundaries of the region of interest and a second copy of the image data contained within the boundaries of the region of interest, the first copy of the image data and the second copy of the image data simultaneously displayed in the output image and separated by either an axis of symmetry or an axis of replication;
   (e) moving, by the computer processing device, the boundaries of the region of interest with respect to the medical image and repeating steps (c)-(d) so that as the output image changes with each movement of the boundaries of the region of the interest, a position of a nodule appearing in the displayed first copy of the image data changes in a synchronized manner with respect to a position of the same nodule simultaneously appearing in the displayed second copy of the image data.

2. The method of claim 1 and further comprising:
identifying presence and location of the nodule from the output image containing the displayed first copy of the image data and the displayed second copy of the image data contained within the boundaries of the region of interest.

3. The method of claim 1, wherein the first copy of the image data includes original image data contained within the boundaries of the region of interest, and wherein the second copy of the image data includes a mirror image based on the image data contained within the boundaries of the region of interest.

4. The method of claim 1, wherein the first copy of the image data includes original image data contained within the boundaries of the region of interest, and wherein the second copy of the image data includes a replicated image based on the image data contained within the boundaries of the region of interest.

5. The method of claim 1, wherein the boundaries of the region of interest are moved a series of times and the output image displayed is an animated display based on the series.

6. A method for detection of nodules in a medical image, the method comprising:
   a) receiving, by a computer processing device, image data representing the medical image;
   b) receiving, by the computer processing device, a selection of a region of interest in the medical image;
   c) copying, by the computer processing device, the image data contained within boundaries of the region of interest;
   d) modifying, by the computer processing device, the copy of the image data from within the boundaries of the region of interest;
   e) outputting for display, by the computer processing device, an output image containing a first copy of the modified image data from within the boundaries of the region of interest and a second copy of the modified image data from within the boundaries of the region of interest, the first copy of the modified image data and the second copy of the modified image data simultaneously displayed within the output image and separated by either an axis of symmetry or an axis of replication; and
   f) moving, by the computer processing device, the boundaries of the region of interest with respect to the medical image and repeating steps (c) through (e) so that as the output image changes with each movement of the boundaries of the region of interest, a position of a nodule appearing in the displayed first copy of the modified image data changes in a synchronized manner with respect to a position of the same nodule simultaneously appearing in the displayed second copy of the modified image data.

7. The method of claim 6, wherein outputting for display the output image containing the first copy of the modified image data and the second copy of the modified image data from within the boundaries of the region of interest includes adding padding pixels to the perimeter of the display.

8. The method of claim 6, wherein the second copy of the modified image data includes a mirror image of the modified image data contained within the boundaries of the region of interest.

9. The method of claim 6, wherein the second copy of the modified image data includes a replicated image of the modified image data contained within the boundaries of the region of interest.

10. The method of claim 6, wherein the boundaries of the region of interest are moved a series of times and the image displayed is an animated display based on the series.

11. The method of claim 6, wherein modifying the copy of the image data from within the boundaries of the region of interest includes using the equation:

$$\text{output}=(\text{input}-A)*B+C$$

where:
output=value of a pixel in the modified image,
input=value of a corresponding input pixel in the input image,
A=a user defined constant,
B=a user defined constant,
C=a user defined constant.

12. The method of claim 11, wherein
   a. A equals a mean pixel value within a region around the input pixel, and
   b. B equals 2.5, and
   c. C equals a mean pixel value of an entire input image times 0.9.

13. The method of claim 12, wherein the region around the input pixel is centered over the input pixel and has an area equal to the square of the width of the region of interest.

14. The method of claim 11, wherein
   a. A equals a minimum pixel value within region around the input pixel, and
   b. B equals a maximum pixel value within a region around the input pixel minus the minimum pixel value within the same region around the input pixel, the sum of which is divided by the sum of the maximum pixel value of the input image minus the minimum pixel value of the input image, and
   c. C equals the minimum pixel value of the input image.

15. The method of claim 11, wherein
   a. A is combined with a value derived from the pixel values in a first region around the input pixel, and
   b. B is combined with a value derived from the pixel values in a second region around the input pixel, and
   c. C is combined with a valued derived from the pixel values in a third region around the input pixel.

* * * * *